(12) United States Patent
Parkhurst et al.

(10) Patent No.: US 8,868,353 B2
(45) Date of Patent: Oct. 21, 2014

(54) SYSTEM AND METHOD FOR TESTING AUTOVERIFICATION RULES

(75) Inventors: Jason Parkhurst, Westfield, IN (US); Kathleen M. Payne, Indianapolis, IN (US)

(73) Assignee: Beckman Coulter, Inc., Brea, CA (US)

( * ) Notice: Subject to any disclaimer, the term of this patent is extended or adjusted under 35 U.S.C. 154(b) by 1043 days.

(21) Appl. No.: 11/701,708

(22) Filed: Feb. 2, 2007

(65) Prior Publication Data

US 2008/0186134 A1 Aug. 7, 2008

(51) Int. Cl.
*G06Q 50/00* (2012.01)
*G06F 19/00* (2011.01)

(52) U.S. Cl.
CPC .................................. *G06F 19/366* (2013.01)
USPC ................................................ 702/22; 705/2

(58) Field of Classification Search
USPC ...................... 600/300; 705/2, 3; 702/22, 182
See application file for complete search history.

(56) References Cited

U.S. PATENT DOCUMENTS

| | | | |
|---|---|---|---|
| 5,005,119 A | | 4/1991 | Rumbaugh et al. |
| 5,005,143 A | | 4/1991 | Altschuler et al. |
| 5,703,788 A | | 12/1997 | Shei et al. |
| 5,732,277 A | | 3/1998 | Kodosky et al. |
| 5,786,816 A | | 7/1998 | Macrae et al. |
| 5,835,384 A | | 11/1998 | Lin |
| 5,850,221 A | * | 12/1998 | Macrae et al. ................ 715/853 |
| 6,063,132 A | | 5/2000 | DeCamp |
| 6,071,236 A | * | 6/2000 | Iliff .............................. 600/300 |
| 6,242,013 B1 | | 6/2001 | Luhman et al. |
| 6,394,811 B2 | * | 5/2002 | Finitzo et al. ................. 434/262 |
| 6,426,759 B1 | * | 7/2002 | Ting et al. ..................... 715/763 |
| 7,315,825 B2 | * | 1/2008 | Rosenfeld et al. ............... 705/2 |
| 7,337,432 B2 | * | 2/2008 | Dathathraya et al. ......... 717/125 |
| 7,461,079 B2 | * | 12/2008 | Walker et al. ................ 707/102 |
| 8,112,232 B2 | | 2/2012 | Parkhurst et al. |
| 8,554,480 B2 | * | 10/2013 | Grigsby et al. .................. 702/2 |
| 2002/0128802 A1 | * | 9/2002 | Rompala ..................... 702/188 |

(Continued)

FOREIGN PATENT DOCUMENTS

| | | |
|---|---|---|
| EP | 0962872 A2 | 12/1999 |
| WO | WO 98/45679 A1 | 10/1998 |
| WO | WO 03/025585 A1 | 3/2003 |

OTHER PUBLICATIONS

"Rules Manual: Instrument Manager v8.05", Data Innovations. Inc., © 1994-2006, 126 pages.

(Continued)

*Primary Examiner* — Sujoy Kundu
*Assistant Examiner* — Ricky Ngon
(74) *Attorney, Agent, or Firm* — Merchant & Gould P.C.

(57) ABSTRACT

A method of testing an autoverification rule comprises providing a rule check including a example test result. After the rule check is provided, the autoverification rule is automatically performed on the rule check. Performance of the autoverification rule on the rule check provides a rule check output. It is then determined whether the rule check output is an expected output. A system for testing the autoverification rules comprises a graphical user interface configured to display an autoverification rule and receive the rule check for the autoverification rule. The system further includes a processor configured to automatically perform the autoverification rule on the rule check and provide a rule check output. The processor is further configured to receive an input indicating whether the rule check output is an approved output for the autoverification rule.

20 Claims, 16 Drawing Sheets

(56) References Cited

U.S. PATENT DOCUMENTS

| | | | |
|---|---|---|---|
| 2003/0139903 A1* | 7/2003 | Zweig et al. | 702/182 |
| 2003/0167265 A1* | 9/2003 | Corynen | 707/4 |
| 2003/0191667 A1* | 10/2003 | Fitzgerald et al. | 705/2 |
| 2004/0030578 A1 | 2/2004 | Cross et al. | |
| 2004/0033164 A1 | 2/2004 | Naito | |
| 2004/0209375 A1 | 10/2004 | Diby et al. | |
| 2005/0066263 A1* | 3/2005 | Baugher | 715/500 |
| 2006/0136263 A1* | 6/2006 | Fry et al. | 705/2 |

OTHER PUBLICATIONS

PCT International Search Report and Written Opinion in Application No. PCT/US08/52568, mailed Jul. 14, 2008, 5 pgs.

European Extended Search Report in Application No. 08728638.1, mailed Jul. 7, 2011, 7 pgs.

* cited by examiner

SYSTEM AND METHOD FOR TESTING AUTOVERIFICATION RULES

CROSS-REFERENCE TO RELATED APPLICATIONS

This application is related to U.S. patent application Ser. No. 11/701,677, entitled "System and Method for Autoverifying Laboratory Test Results", which was also filed on Feb. 2, 2007.

FIELD

This disclosure relates to the field of laboratory testing, and particularly clinical diagnostic testing and pre-clinical testing and verification of related laboratory test results.

BACKGROUND

Clinical diagnostic tests are commonly used in the medical profession to assist in diagnosing various medical conditions of a patient. Clinical diagnostic tests refer to those tests where a laboratory conducts an analysis on a specimen/sample from a patient. The term "sample" or "specimen" as used herein is intended to refer to such substances taken from a body including, without limitation, blood, urine, tissue, saliva, or other body substances. Following analysis of the patient sample, the laboratory produces a test result. The test result is then used by the doctor or other medical professional to assist in the diagnosis of one or more medical conditions.

In addition to clinical diagnostic testing, specimens may also be analyzed in other environments, such as pre-clinical testing. Pre-clinical testing refers to situations where drugs or devices are tested in a laboratory setting using various samples. For example, a new drug may be administered to a patient, and the patient's blood may be monitored to determine the effects of the drug on the patient. The term "clinical test result" as used herein is intended to refer to test results produced from clinical diagnostic testing and/or pre-clinical testing.

In a hospital lab, a test order for a clinical diagnostic test is delivered from a doctor and received in the laboratory accompanied by a patient sample. The patient sample is analyzed on one or more laboratory instruments to obtain test results. Examples of laboratory analyzers used to analyze patient samples include flow cytometers, hematology analyzers, immunoassay analyzers, and electrophoresis analyzers. It will also be recognized that numerous other laboratory analyzers may be used to analyze patient samples. Furthermore, manual testing may also be performed on the sample by a laboratory technician to provide test results for the test order. Once a sample is analyzed in the laboratory, the fulfilled test order is sent back to the doctor in the form of a test result. In many environments, the test order is received electronically and the test results are reported electronically through a local area network which provides access to various information systems.

The release of actual test results from the clinical diagnostic laboratory is typically staged. In particular, "raw" test results from the laboratory analyzer are typically held in the laboratory's own database and computer system, often referred to as the laboratory information system ("LIS"). These raw test results are typically not released for viewing outside of the laboratory until they are approved by the lab. As mentioned above, raw test results may be approved automatically or manually following review by a lab technician. Once test results are approved, the test results are released to a hospital or other medical facility's database and computer system, often referred to as the hospital information system ("HIS"). Doctors and other care providers have access to the approved test results in the HIS, but only the laboratory staff has access to unapproved results in the LIS.

Accordingly, one task for the laboratory technician performing or overseeing clinical diagnostic tests is to validate the test results obtained from the laboratory analyzers or from manual testing before they are released to various information systems. The need for validation is present because many problems can occur during the sample gathering and testing process. For example, a patient sample may be mislabeled, resulting in test results being reported in association with the wrong patient. As another example, the patient sample may have been improperly drawn or improperly handled, resulting in sample contamination and erroneous test results. Furthermore, a laboratory analyzer may be either malfunctioning or drifting out of calibration, again causing the analyzer to report erroneous results.

Abnormal test results do not necessarily indicate erroneous results, but may instead indicate a serious medical problem. In such cases, it may be important for the lab technician to report the test results immediately to the doctor or other medical professional in addition to the normal reporting procedure of making the test results electronically available through a database. In these situations, the test results indicating a critical condition may call for the lab technician to make an immediate and confirmed report to the doctor, such as by telephone or in person.

Evaluating test results can, in many cases, be done automatically by a computer. This process of using a computer to automatically evaluate laboratory test results is called autoverification (or autovalidation). Using autoverification, a test result from a laboratory analyzer is sent to a computer for evaluation. If the computer determines that the test result meets predetermined criteria established by the laboratory, the test result is approved and automatically released to the doctor. Test results that fail autoverification are held for manual review by the lab technician. Upon manual review, the lab technician may decide upon certain actions, such as releasing the test result, calling for a new test, calling for a new patient sample, calling for service on the laboratory analyzer, requesting confirmation of input data, or various other actions.

Existing laboratory information systems attempt to provide autoverification capabilities by having the user write a series of "if/then" rules that are evaluated by the computer when test orders are received, test results are obtained, and/or results are uploaded to the HIS. These if/then rules essentially amount to a text-based programming language where the user is expected to write the complete autoverification process with the provided language. However, laboratory technicians are not typically trained in computer programming skills and find it difficult to write the autoverification rules based on the common text-based language. In addition, even for accomplished programmers, the provided language is typically awkward, and it is easy for the programmer to neglect certain aspects of the desired autoverification rule which is displayed as a confusing list of textual statements. Furthermore, once an autoverification process is defined using such systems, it is difficult for a laboratory technician to pull the defined autoverification process at a later time and easily determine the workflow within the process, since the series of textual "if/then" statements are difficult to follow. Accordingly, it would be advantageous to provide an autoverification system where autoverification processes created using the system are easily defined by the user and quickly and easily understood when presented to the user at a later time.

In addition to the awkward language used to define autoverification rules, existing systems also do not assist the technician in checking the correctness of autoverification rules. Before autoverification rules are used in the laboratory, they are typically hand checked to determine if the rules are correct and will operate as expected. In order to determine if an autoverification rule is correct, a lab tech will provide several example inputs, and work through the autoverification rule to arrive at a result based on the example input. The user must then decide whether the rule provides an unexpected result based on the example input. If an unexpected result is obtained, this indicates a potential problem with the autoverification rule as defined. This process of hand checking autoverification rules is tedious and subject to human error, as the lab technician works through the autoverification rule one example input at a time. In particular, if the user does not follow the rule precisely, the outcome determined by the user for a particular rule check may be entirely different than the actual outcome under the rule. Accordingly, it would be advantageous to provide a system for testing autoverification rules that is accomplished automatically, thus relieving the laboratory technician of the burden of manually checking autoverification rules while also providing a systematic process for rule testing.

Another problem with current rule checking processes is the difficulty in confirming that all possible steps through the rule have been checked. With the current rule checking processes, it is easy for the lab technician to forget about certain steps within the autoverification rule and forget to provide and test example inputs that move through these steps. Accordingly, it would be advantageous to provide a system for testing autoverification rules that includes a tool for ensuring that all possible steps through the defined autoverification rule have been tested.

Furthermore, if an autoverification rule is modified following initial rule checking, current systems provide no support for regression testing of the rule. In other words, when an autoverification rule is modified, no tools are provided to assist the user in seeing different outcomes based on the changes to the rule. This means that all previous rule checking for a particular autoverification rule must be redone whenever there is a modification to the rule. Accordingly, it would be advantageous to provide a system for testing autoverification rules that includes a tool for retesting a modified rule without the need to completely redo the original rule testing.

Yet another need with current systems for testing autoverification rules is the ability to easily document rule testing. In many laboratories, rule checking is mandatory before the rule may be used in the laboratory. With current systems, hand written notes are the only available proof of rule checking. Therefore, it would be advantageous to provide a system for testing autoverification rules where the testing procedure may be easily documented, thus providing proof that the autoverification rules have been properly tested.

SUMMARY

A method of testing at least one autoverification rule configured to autoverify laboratory test results is disclosed herein. According to at least one embodiment, the method comprises first providing a rule check including a sample input. After the rule check is provided, the autoverification rule is automatically performed on the rule check. Performance of the autoverification rule on the rule check provides a rule check output. It is then determined whether the rule check output is an expected output.

A system for testing the autoverification rules is also disclosed herein. According to at least one embodiment, the system includes a graphical user interface configured to display an autoverification rule and receive a rule check for the autoverification rule. The rule check includes an example test result. The system further includes a processor configured to automatically perform the autoverification rule on the rule check and provide a rule check output. The processor is further configured to receive an input indicating whether the rule check output is an approved output for the autoverification rule.

In at least one embodiment, the system disclosed herein provides a plurality of different environments related to the autoverification rule. The plurality of environments comprise an editor environment configured to define the autoverification rule. The plurality of environments further comprise a rule check environment configured to receive a rule check including an example test result. The rule check environment is further configured to perform the autoverification rule based on the rule check and determine whether performance of the autoverification rule based on the rule check provides an expected output. The plurality of environments also comprise a laboratory environment configured to perform the autoverification rule on actual clinical test results.

The above described features and advantages, as well as others, will become more readily apparent to those of ordinary skill in the art by reference to the following detailed description and accompanying drawings.

DESCRIPTION

Exemplary System Arrangement

Figure 1:
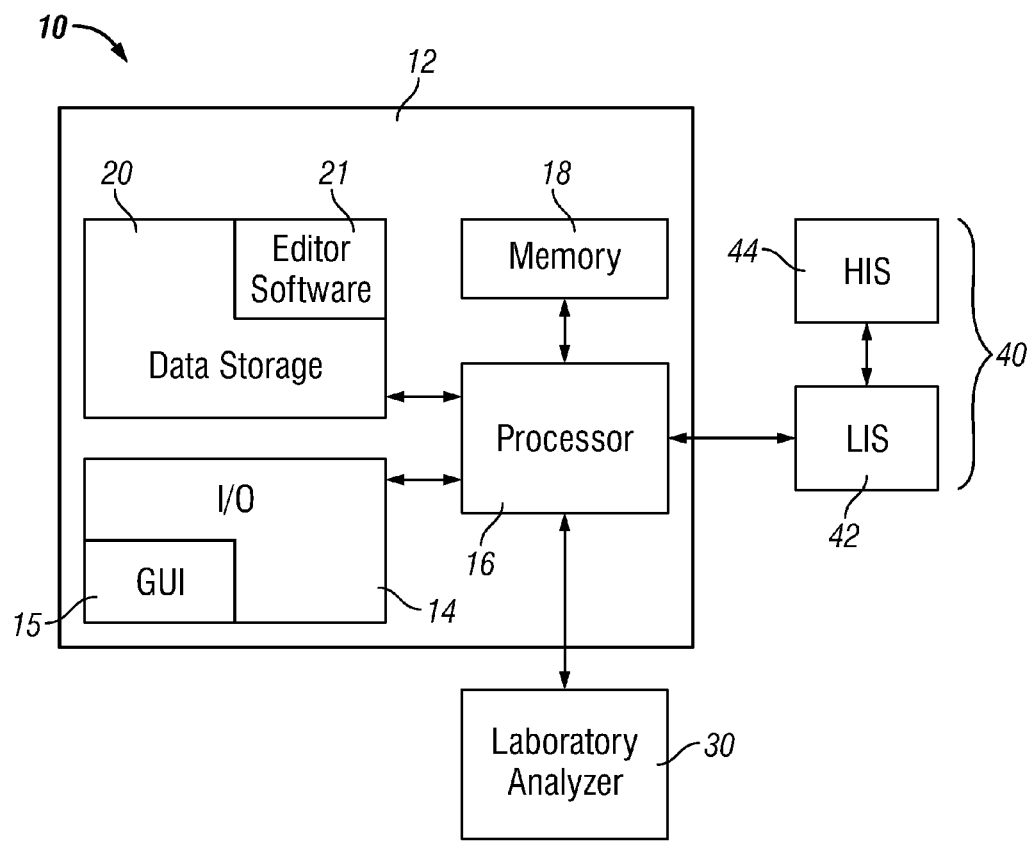
FIG. 1 shows a block diagram of a system for autoverifying laboratory test results, including a graphical user interface.

With reference to FIG. 1, an exemplary system for autoverifying laboratory test results is shown. The system 10 is provided as a computer 12 including input/output devices 14, a processor 16, a memory 18, and data storage 20. The computer 12 is connected to a laboratory analyzer 30. The computer 12 and the laboratory analyzer 30 are also connected to a network 40. The network 40 includes a laboratory information system (LIS) 42 and a hospital information system (HIS) 44 in communication with the LIS. The LIS and HIS include databases configured to retain test results available for viewing through either the HIS or the LIS, as permission to view the test results is granted by the system.

When a test order is received in the clinical laboratory, it is accompanied by a patient sample. The laboratory analyzer 30 is configured to perform a test on the patient sample and provide a test result that may be used for clinical diagnostic purposes. Exemplary laboratory analyzers include hematology analyzers, flow cytometers, immunoassay analyzers, protein analyzers, and electrophoresis analyzers. However, it will be recognized that any of numerous other laboratory analyzers capable of analyzing a sample and providing a test result may also be utilized. Manual testing may also be performed on the sample, such as viewing tissue under a microscope, and the results of such analysis may be manually entered into the system. In addition, while only a single laboratory analyzer 30 is shown in FIG. 1, it will be recognized that a plurality of laboratory analyzers may be connected to the computer and configured to provide test results to the computer. While the laboratory analyzer of FIG. 1 is shown connected directly to the computer 12, the laboratory analyzer 30 may instead be connected to a network along with other analyzers. For example, the laboratory analyzer 30 may be connected to the LIS 42, and test results from the laboratory analyzer may be reported to the computer through the LIS 42.

The computer 12 includes various input/output devices 14 configured to communicate with the lab technician or other operator/user. For example, one output device is a graphical user interface 15 which comprises a screen capable of displaying graphical images to the operator. Exemplary graphical user interfaces 15 comprise CRT screens and LED screens. The computer 12 further comprises various input devices 14, such as a mouse, touchscreen, keyboard, etc., which allow the operator to provide inputs to the computer 12.

The processor 16 is in communication with the input/output devices 14 and generally controls the flow of data within the computer, processes various instructions, and performs calculations. The processor 16 is further connected to the memory 18, and the data storage device 20, such as a hard drive. Software programs are stored on the data storage device 20 and memory 18, and the instructions provided by the software programs are executed by the processor 16.

Creating and Editing Autoverification Rules/Editor Environment

One software program stored on the computer 12 is an autoverification rule editor 21. The editor software 21 works in association with the processor 16 and the graphical user interface 14 and allows the user to easily create autoverification processes (also referred to herein as "autoverification rules"). In particular, the editor 21 uses a flowchart-based language which allows the user to create autoverification rules as flowcharts. As discussed previously, autoverification rules are configured to evaluate test results provided by the laboratory analyzer 30 and determine if the laboratory test results meet certain predetermined criteria established by the laboratory.

Figure 2:
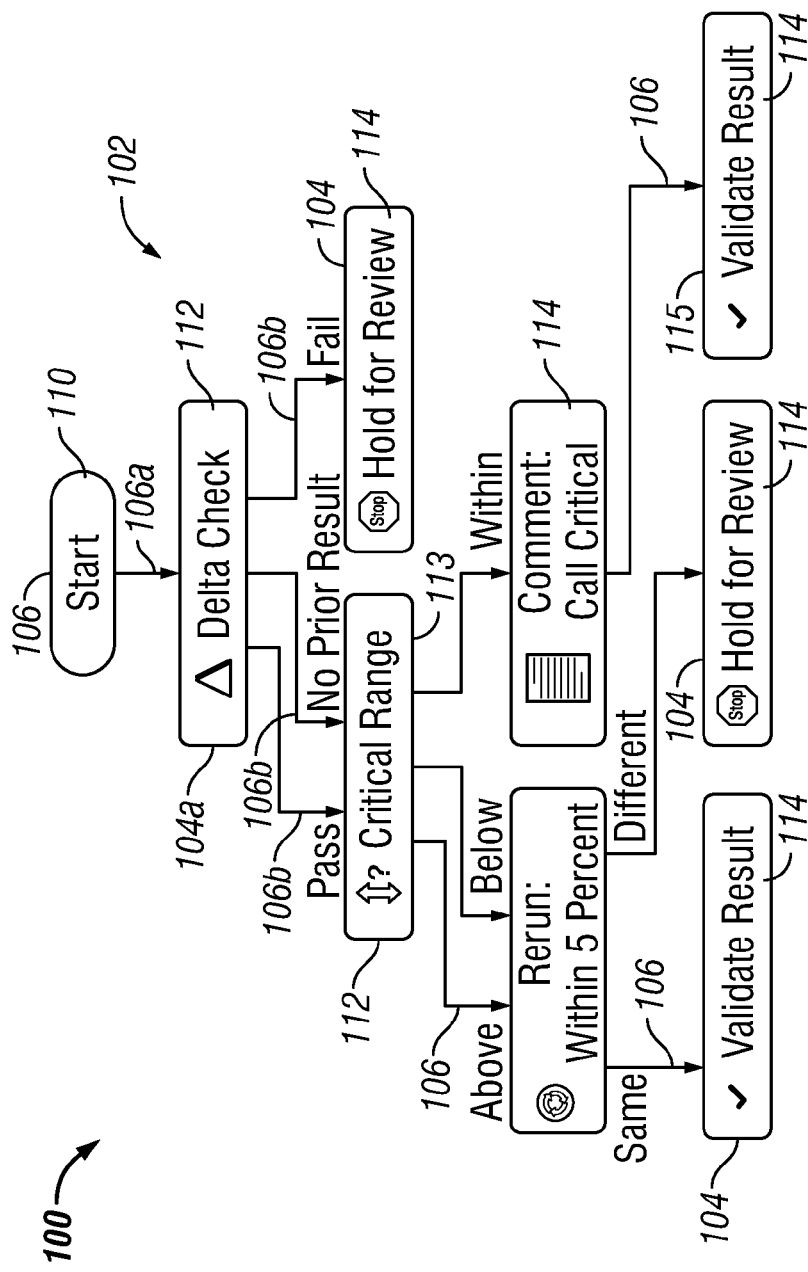
FIG. 2 shows an exemplary autoverification process in the form of a flowchart created using the system of FIG. 1.

With reference now to FIG. 2, an exemplary autoverification rule 100 created with the editor is shown as seen by the user on the graphical user interface 14. The term "autoverification rule" or "autoverification process" as used herein references the instructions and processes used to evaluate laboratory test results as well as the workflow involved with the evaluation process. Accordingly, an autoverification rule test comprise instructions to perform testing or take some other action on a sample in addition to evaluating test results.

In FIG. 2, the autoverification rule 100 is displayed in the form of a flowchart 102. The flowchart 102 provides a schematic representation of the autoverification rule and comprises a plurality of nodes 104 and a plurality of edges 106 connecting the nodes. Some action, instruction or analysis occurs at each node 104. The edges 106 define a workflow between the plurality of nodes 104, showing the direction of progress from one node to another node within the flowchart 102. Accordingly, a given node (e.g., node 104a) may be connected to input edges 106a indicating progress into the node and/or output edges 106b indicating progress out of the node. If more than one output edge 106b extends from a node 104, the output edges 106b extending from the node 104 will also indicate a contingency required before following the edge (e.g., "pass", "fail", "above", "below", etc.).

The nodes 104 are shown as box-like structures in the embodiment of FIG. 2, but it will be recognized that the nodes 104 may also be displayed in other forms. Similarly, the edges 106 are shown as arrow-like symbols in FIG. 2, but it will be recognized that the edges 106 may also be displayed in other forms.

The nodes 104 available for use in building a flowchart using the editor comprise start nodes 110, decision nodes 112, and action nodes 114. Each autoverification rule includes one start node 110. Execution of the autoverification rule begins with the start node 110. An exemplary start node 110 is shown in FIG. 2 at the top of the flowchart 100.

Decision nodes 112 are those nodes where a decision is made to proceed to one of a plurality of other nodes based on an input. For example, a decision node may check information provided about a patient, a specimen from the patient, one or more test results from a laboratory analyzer, or other information. After analyzing the input, the node determines a process flow based on the input information. Accordingly, each decision node includes two or more output edges 106b.

An exemplary decision node 112 shown in FIG. 2 is the range node 113. As described in further detail below, a range node 113 is configured to determine whether an input is above a predetermined range, below a predetermined range, or within a predetermined range. Accordingly, the range node 113 includes three output edges, each indicating a path to a different node depending upon whether the input is above the given range, below the given range, or within the given range.

Action nodes 114 are those nodes where some action, notice, or other side-effect occurs in the system as a result of execution of the node. For example, an action node may comprise validating a test result, releasing a test result to a higher level information system, holding a test result for review by a technician, adding a comment to a test result, ordering a dilution or test rerun, canceling a test, or calculating test results. Accordingly, action nodes are available to define the workflow associated with a particular autoverification rule, such as the ordering of tests, dilutions, or reruns. Action nodes may have one or more input nodes, but have only one or zero output nodes, as no decisions are made in an action node.

An exemplary action node 114 shown in FIG. 2 is the validate result node 115. When execution of the autoverification rule 100 reaches the validate result node 115, the system has evaluated the test result and confirmed that it meets certain predetermined criteria. At this point, the test result may be released to a higher level information system, where before validation the test result was only available to laboratory personnel using the laboratory information system. Following validation and release of the test result to the higher level information system, the test result may be viewed by medical personnel, such as doctors, on the hospital information system.

Figure 3:
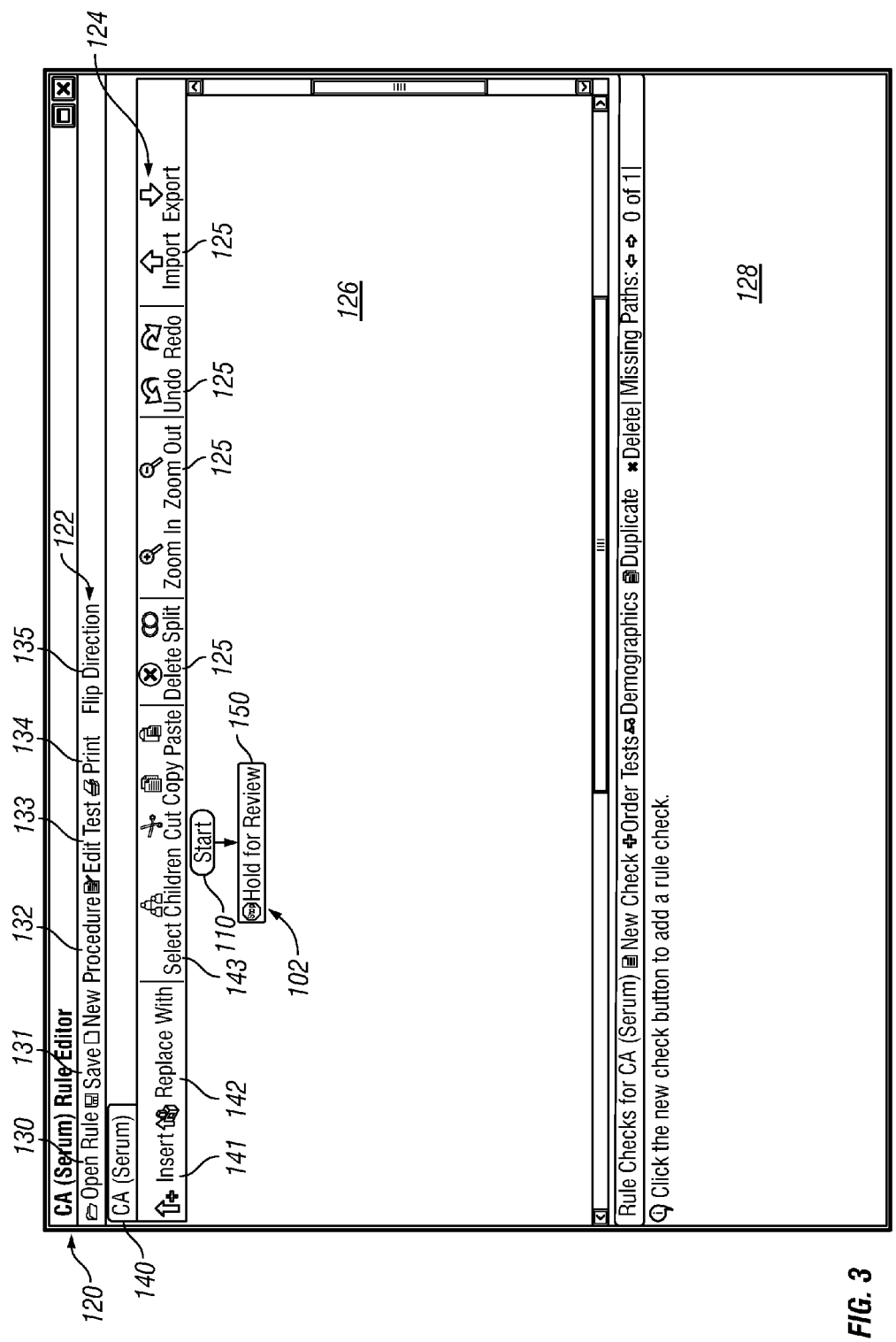
FIG. 3 shows an exemplary flowchart for an autoverification process displayed on a screen of the graphical user interface of FIG. 1.

Use of the editor to create autoverification rules in an exemplary editor environment for the system is now described with reference to FIGS. 3-8. FIG. 3 shows an embodiment of the editor 120 as may be seen on the screen of the graphical user interface. The editor 120 comprises a top menu 122, a toolbar 124, a rule builder window 126, and a rule check window 128.

The top menu 122 of the editor provides the user with access to various options 130-135. For example, when the "open rule" option 130 is selected, the user may open a rule from one of the system folders. Other options listed on the top menu include the "save" option 131, "new procedure" option 132, "edit test" option 133, "print" option 134, and "flip direction" option 135. The tab 140 just below the top menu 122 indicates the autoverification rule shown in the rule builder window 126. As shown by the tab 140, the autoverification rule currently displayed in the rule builder window 126 of FIGS. 3-8 is for the serum calcium test.

The toolbar 124 is provided below the top menu 122. The toolbar 124 lists a plurality of options for use by the user when working in the rule builder window 126 and displays the options as buttons 125. In FIG. 3, the toolbar is shown with several buttons, including the "insert" option 141, "replace with" option 142, and "select children" option 143. Each of these options is described in further detail below with respect to the rule builder window 126 and FIGS. 3-8. FIGS. 3-8 also show other options on the toolbar 124, and it will be recognized that these or different options may be provided on the toolbar in various embodiments as determined by the user.

As mentioned above, the editor's rule builder window 126 displays a selected autoverification rule 100 in flowchart form 102. The autoverification rule 100 displayed in the rule builder window 126 may be saved, edited, or executed. As explained in further detail below, execution of an autoverification rule results in automation of the workflow for the associated test order.

With continued reference to FIG. 3, assembly and editing of an autoverification rule begins when the "open rule" option 130 is selected from the top menu 122. When this option 130 is selected the selected rule appears in the rule builder window 126. The selected rule may be as simple as a start node connected to a run procedure node. In any event, the user may edit the rule in the rule builder window 126. Additional nodes may be obtained by selecting the "insert" option 141 on the toolbar 124. Upon selecting the "insert" option 141, the user is presented with a drop down menu of nodes that may be used in the rule. The drop down menu associate with the "insert" option 141 includes a list of various decision nodes, various action nodes, and a start node. In order to insert a node 110 in the rule builder window 126, the user simply clicks on the node selection from the drop down menu, and the selected node appears in the rule builder window. To connect a selected node 110 to another node existing in the rule builder window 126, the user clicks on the selected node 110 and drags it to make the desired connection to another node within the window.

Figure 4:
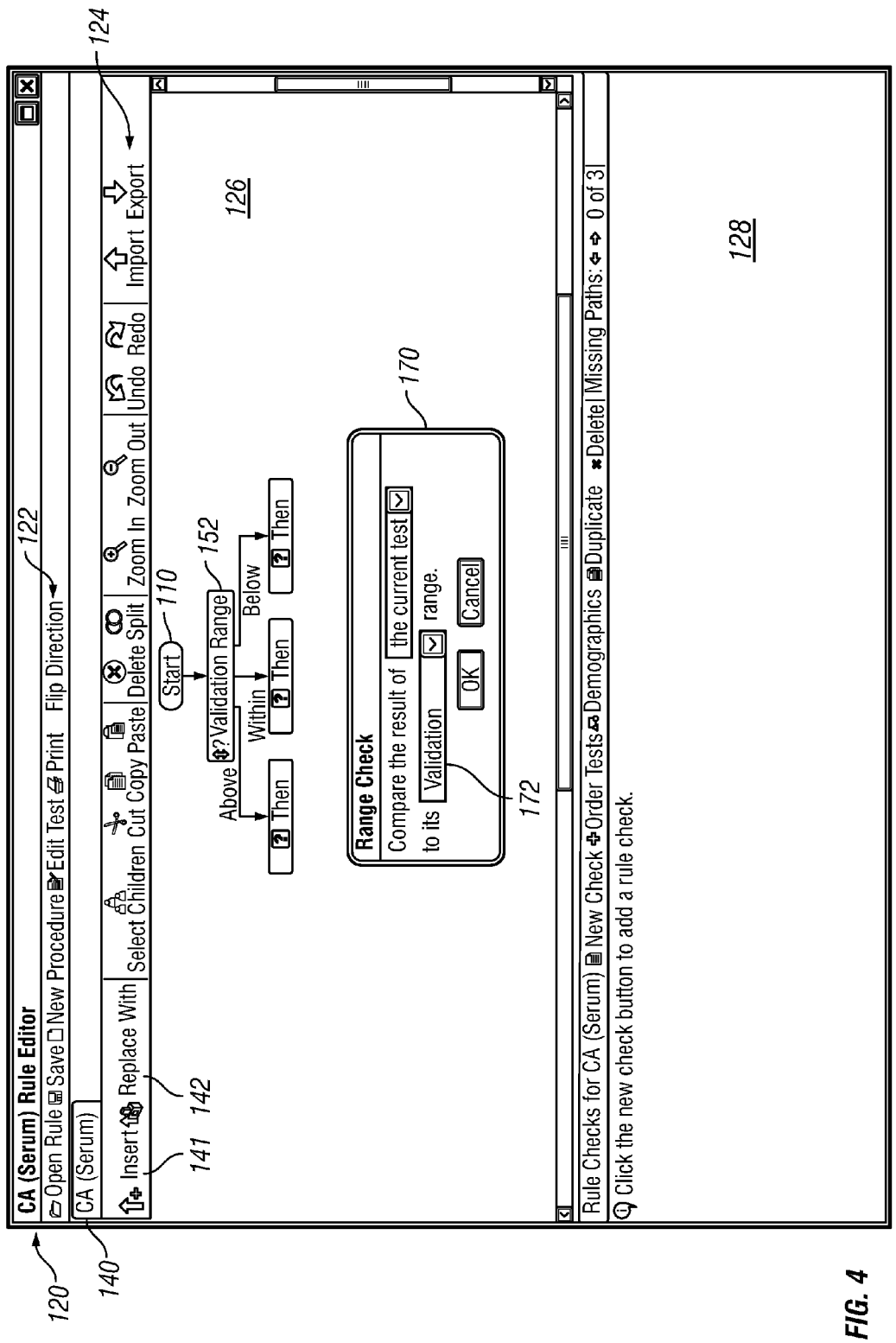
FIG. 4 shows the exemplary flowchart of FIG. 3 with an exemplary configuration box displayed on the screen along with the flowchart.
Figure 5:
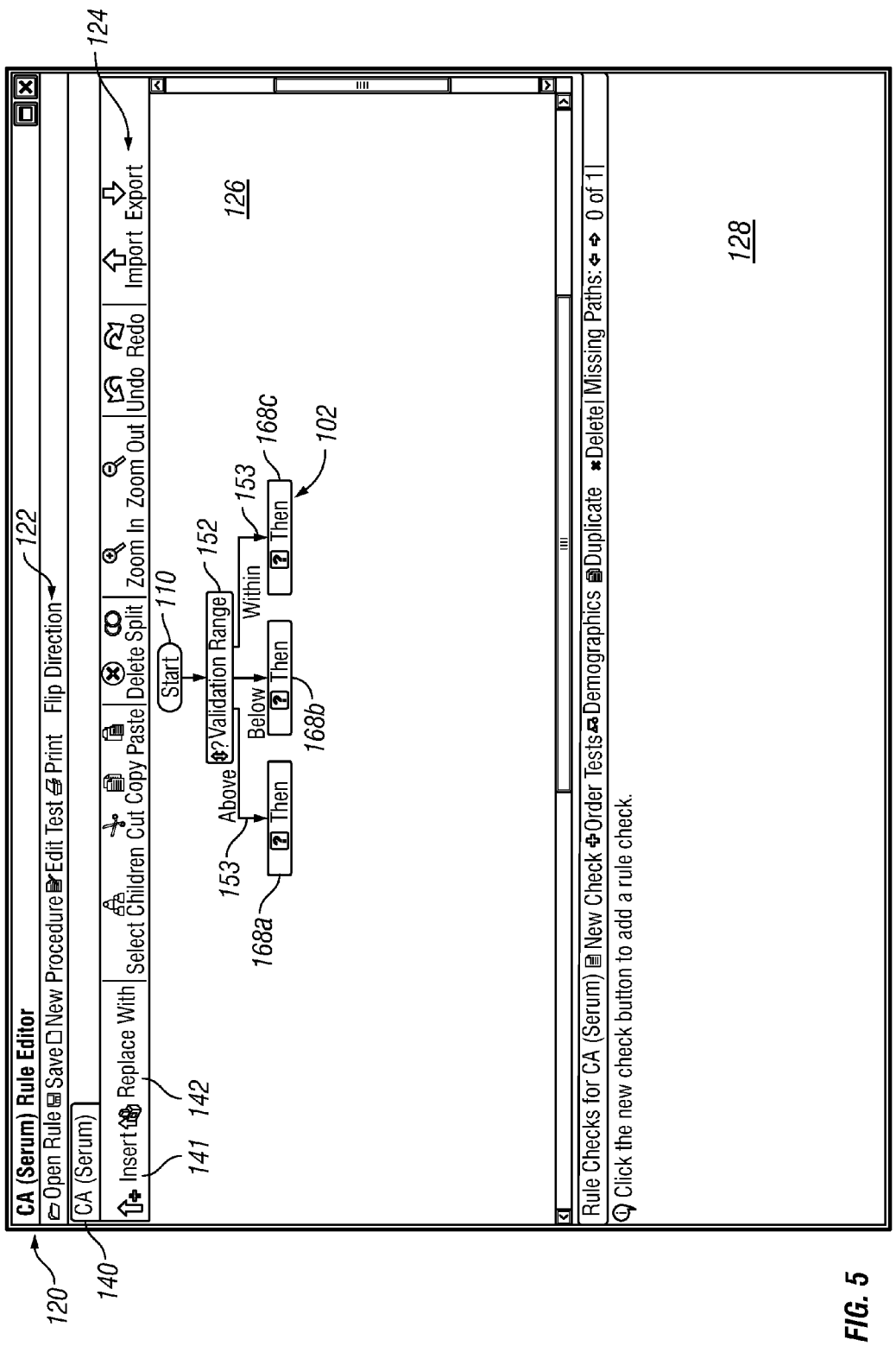
FIG. 5 shows the exemplary flowchart of FIG. 4 with a decision node having a plurality of output edges.

In FIG. 3, the user has inserted a hold node 150 in the rule builder window 126 and connected it to the start node 110. In addition to inserting nodes, the user may easily replace a node inserted into the rule builder window with a different node. In order to do this, the user first clicks on the node to be replaced in the rule builder window. When a node is selected by clicking on the node, the node is highlight in the rule builder window. After highlighting the node to be replaced in the rule builder window, the user selects the replace option 142 on the toolbar. Upon selecting the replace option, the user is provided with another list in the form of a drop down menu of available nodes for insertion in the rule builder window. By selecting a node from the provided drop down menu, the highlighted node in the rule builder window is replaced with the selected node. In the example provided, the user has highlighted the hold node 150 in FIG. 3, and the hold node is shown in the rule builder window 126 highlighted with a bold outline. In FIG. 4, the user has selected a range node 152 from the drop down menu associated with the replace option 142, and the hold node 150 (previously shown in FIG. 3) has been replaced by the range node 152.

As described above, when a node is selected from the insert menu 141 or the replace menu 142, the node appears in the rule builder window 126. Certain nodes selected for insertion in the rule builder window will require configuration. When a selected node requires configuration, a configuration box appears in the rule builder window which prompts the user to insert all necessary data required to properly configure the node. For example, as shown in FIG. 4, when the user selects the range node 152, a configuration box 170 appears in the rule builder window 126. The configuration box 170 instructs the user to enter the proper data in order to configure the node. In the example of FIG. 4, the user must configure the range node 152 by specifying a particular test to range check and specifying a particular range for comparison.

In some instances, nodes may be configured in different manners. For example, a range node, such as the one shown in FIG. 4, may be configured based on numerical limits inserted by the user or based on named ranges which are predefined by the laboratory for the particular test. Thus, in some instances the user may insert a numbers in the configuration box to define the lower limit and upper limit for the node. In other instances, the user may select one of several named ranges, each named range having a predefined upper limit and a predefined lower limit. Examples of named ranges include a validation range, a reference range, or a critical range.

When a range node is designed in this manner such that the user is not required to insert specific details (such as numerical values) for the range, it is considered a common node. A common node one in which the node's configuration is independent of the specific test in which the node is used. If specific details are required in association with the configuration of the node for a particular rule, those details are predetermined by the laboratory and are automatically retrieved when the common node is inserted into the rule. Thus, common nodes allow the user to easily build autoverification rules without having to pull specific details related to the test result being analyzed, such as specific acceptable ranges for different test results.

FIG. 4 shows an embodiment where the range node 152 is configured as a common node. In this embodiment of the range node 152, the user configures the node by simply selecting one of several named ranges. The numerical values associated with the named range have already been predefined by the laboratory for the particular test in which they are used. In FIG. 4, the user has selected the "validation range" from the lower drop down menu 172 of the configuration box 170. The validation range is a predefined range determined by the laboratory where test results falling within the range will be considered valid test results for the particular test results being analyzed by the rule. For the serum calcium autoverification rule of FIG. 4, the laboratory may predefine the validation range to be between 2 and 20 mg/dL. This means that the lab considers any test result within this range to be consistent with what can be considered a realistic test result from a serum calcium test. However, if the laboratory receives a result of 50 mg/dL, the system will consider this to be an unrealistic test result for serum calcium, and the lab will assume that some error has been made in the analysis.

Similar to the "validation range", the laboratory may define other ranges, such as a "reference range" or a "critical range" for the range node 152 when used as a common node. For example, the laboratory may define the reference range for serum calcium to be between 9 and 10.5 mg/dL. This means that a serum calcium test result within this range is considered normal, and the test result does not indicate an issue for the patient. As another example, the laboratory may define the critical range for serum calcium to be between 8 and 15 mg/dL. This means that a serum calcium test result outside of the critical range suggests a critical issue for the patient. In this case, the system may be configured to immediately notify the physician of the test result so that immediate attention may be given to the patient. It will be recognized that the above ranges are merely examples of ranges that may be predefined by a laboratory using the system, and numerous other ranges could be defined by the laboratory. Furthermore, while the range node 152 has been described herein as one example node that requires configuration when inserting the node into the rule builder window 126, it will be recognized that many other nodes that may be selected by the user must also be configured before they are properly included into the autoverification rule.

Once a node has been inserted into the rule builder window and configured (if required), outputs from the node must be associated with subsequent nodes. As discussed previously, all decision nodes will have at least two outputs. To assist the user with properly associating the two or more required outputs from a decision node with subsequent nodes, the editor is configured to show each of the possible outputs from a decision node when the decision node is placed in the rule builder window. Accordingly, in the example of FIG. 5, when the range node 152 is placed in the rule builder window 126 the editor immediately displays the range node 152 with three output edges 153 already extending from the node 152. The three output edges 153 extending from the node 152 advantageously remind the user that three possible outcomes may result from a range node. In particular, a range node will compare a test result to the defined range and determine whether the test result is within the defined range, above the defined range, or below the defined range. By displaying an output edge 153 for each of the three possible outcomes, the user is reminded to connect each of the three possible outcomes to a resulting node. To further assist the user, the editor extends each of the three output edges 153 from the range node 152 to a dummy node 168a-168c (i.e., an un-configured "then . . . " node).

Figure 6:
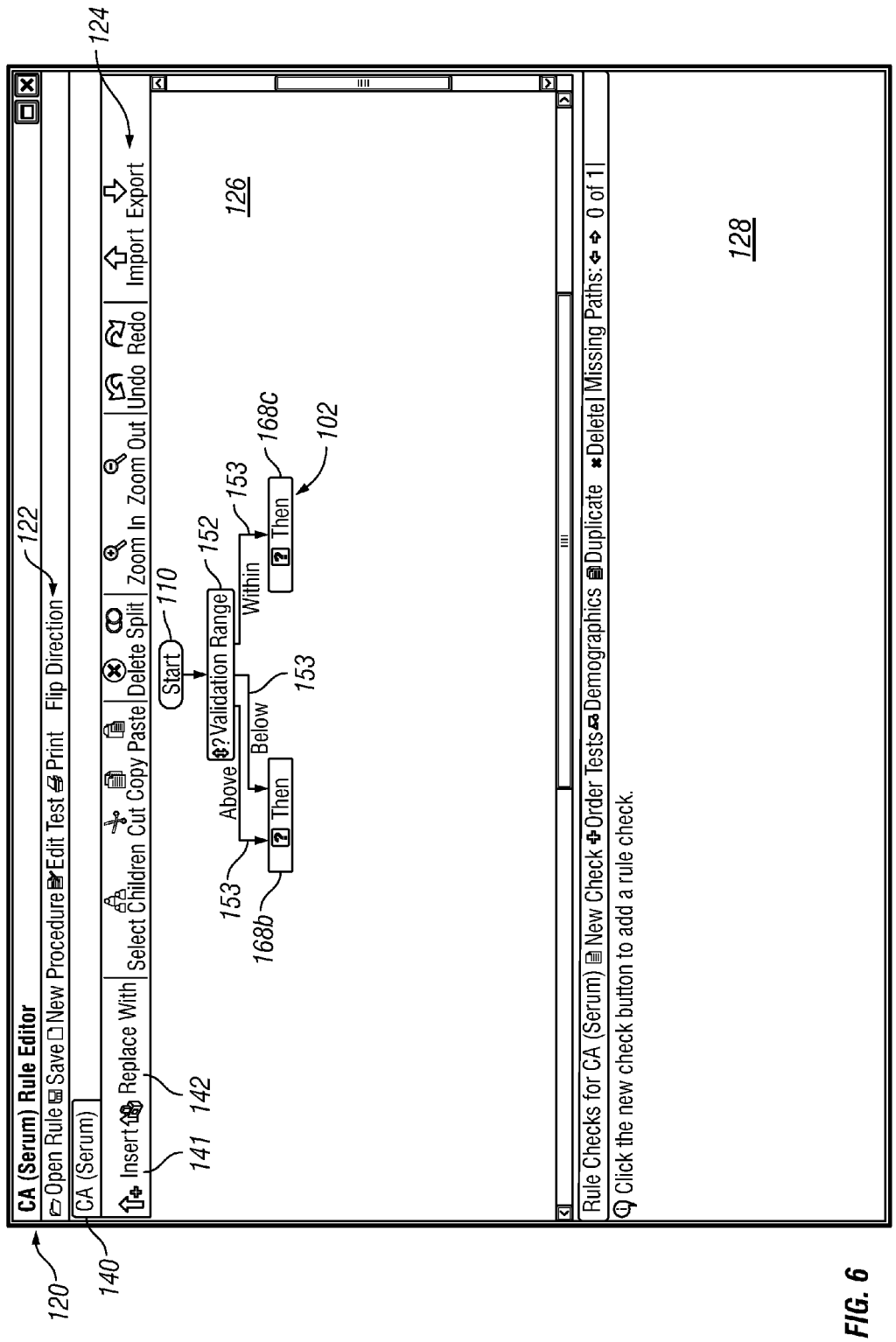
FIG. 6 shows the exemplary flowchart of FIG. 5 wherein one of the output edges of the decision node has been directed to a different node.

The output edges of a decision node which automatically appearing upon the insertion of the decision node into the rule builder window 126 may be manipulated by the user to lead to either two or three nodes. For example, in FIG. 6 the user has manipulated the output edges 153 of the range node 152 to indicate that a test result outside of the validation range leads to a first node 168b, regardless of whether the test result is above or below the validation range, and a test result within the validation range leads to a second node 168c. To accomplish this, the user simply clicks near the arrow on the "above" edge 153 shown in FIG. 5, and drags the edge to the node 168b associated with the "below" edge. The editor then automatically removes the dummy node previously associated with the "above" edge from the rule builder window 126, and both the "above" edge and the "below" edge lead to the same dummy node 168b, as shown in FIG. 6. While manipulation of edges has been described herein with respect to edges leading to dummy nodes, it will be recognized that the editor may allow manipulation of any edges within a partial or complete flowchart in a similar manner. Accordingly, the editor provides a convenient way for users to manipulate flowcharts and the node-to-node progression through the flowchart.

Figure 7:
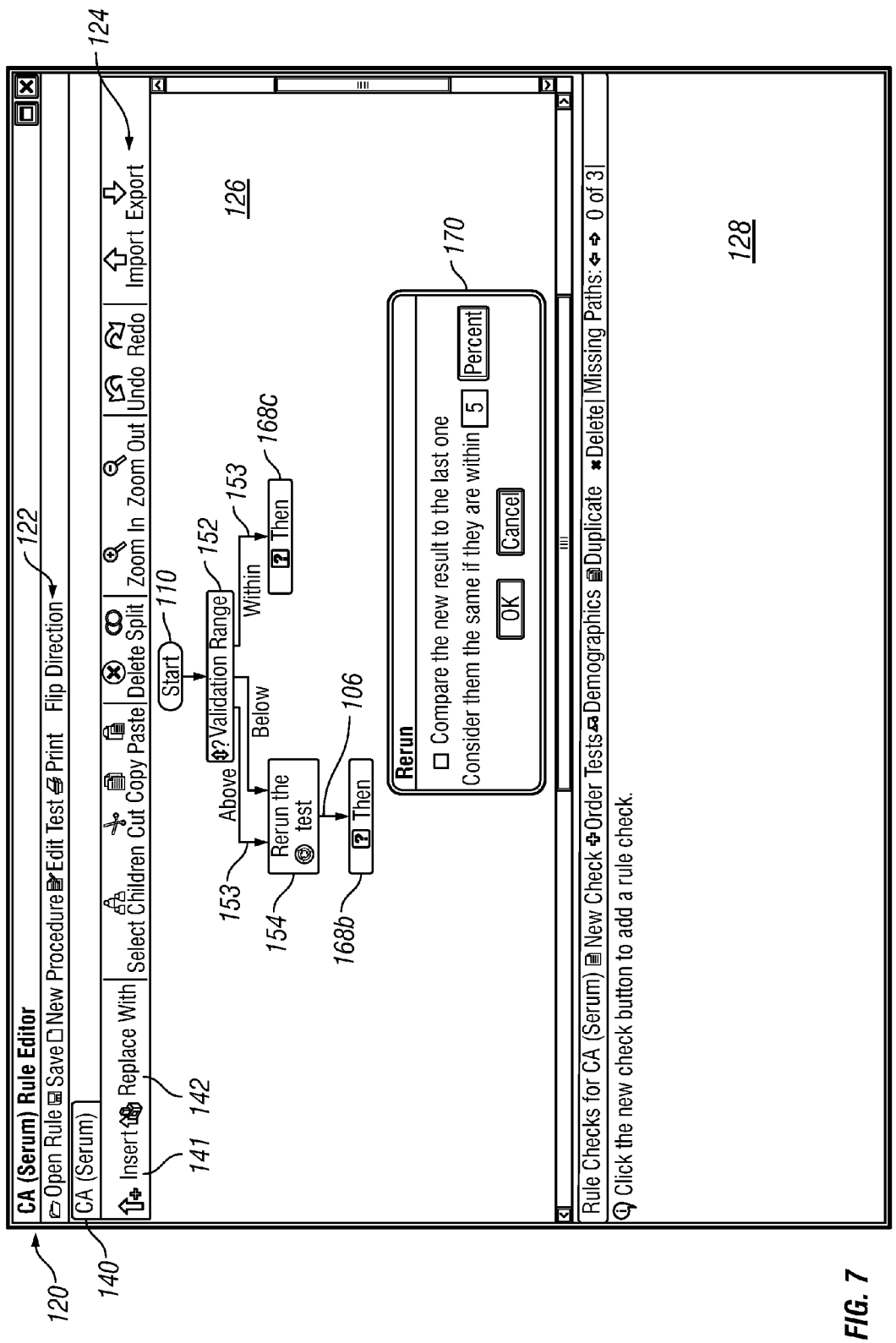
FIG. 7 shows the exemplary flowchart of FIG. 6 with a rerun node added to the flowchart and a dialog box appearing on the screen along with the flowchart.

In addition to manipulating edges within the flowchart 102, the user may also manipulate nodes by inserting new nodes or replacing existing nodes. For example, as shown in FIG. 7, the user had replaced the dummy node 168b in the rule builder window 126 with a functional node 154. This is accomplished using the replace option 142 from the toolbar 124, described above. When using the "replace" option 142, the user first highlights the node to be replaced and then selects the "replace" option 142 from the toolbar. When the "replace" option 142 is selected, the user is presented with a drop-down menu listing various nodes to replace the highlighted node. After the user selects a replacement node from the drop down menu, it automatically appears in the rule builder window 126 in place of the previously highlighted node. In the case of FIG. 7, the user has replaced the dummy node 168b following the above and below edges 153 with a "rerun" node 154.

As shown in FIG. 7, when the user selects the "rerun" node 154 for insertion, a configuration box 170 automatically appears in the rule builder window 126, instructing the user to properly configure the "rerun" node 154. At the same time, a new dummy node 168d is provided in the rule builder window 126 on the output edge 106 of the "rerun" node.

Figure 8:
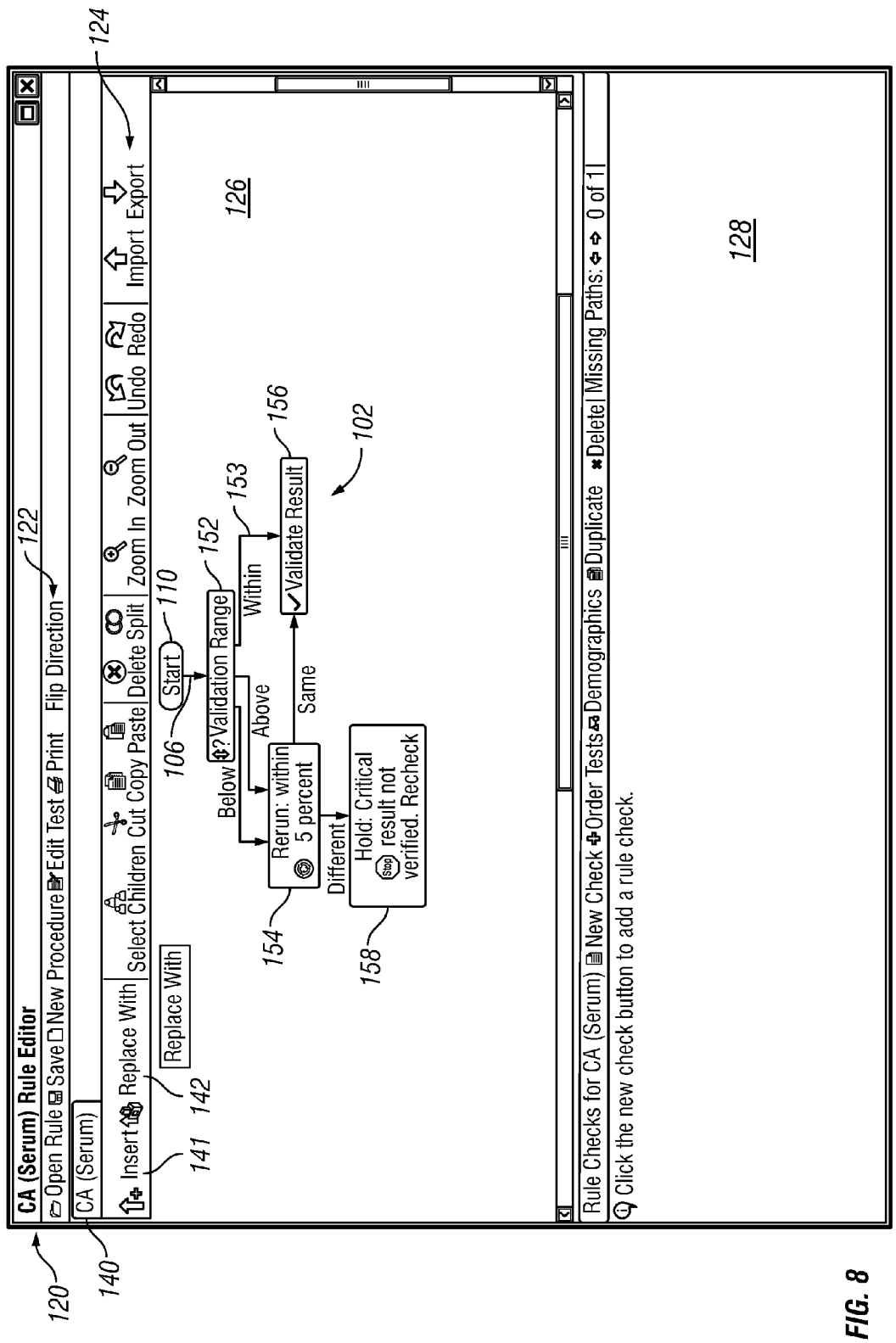
FIG. 8 shows the exemplary flowchart of FIG. 7 including further nodes and directed edges.

FIG. 8 shows that the "rerun" node 154 has been configured by the user. As a result of the configuration, the "rerun" node now includes two output edges, and the node has instructions to compare the rerun test result to the previous test result. Thus, the "rerun" node 154 is an action node that is also configured to make a decision related to the action. In the embodiment of FIG. 8, the user has configured the "rerun" node 154 to rerun the original test result since it fell outside of the validation range. The node 154 has also been configured to compare the new test result following the rerun to the previous test result. As also shown in FIG. 8, if the rerun test result is not within five percent of the previous test result, the rule holds the test result at hold node 158, which indicates that the test result is an invalid test result outside of the validation range and should be manually checked by the user. However, if the rerun test result is within five percent of the previous test result, the rule has been configured to validate the test result at the validate node 156.

As also shown in FIG. 8, the user has clicked the "within" output edge 153 from the range node 152 and dragged it down to the validate node 156. Upon validation, test results are noted as validated within the information system (e.g., the LIS) and may be released for observation in other information systems (e.g., the HIS).

As discussed above with reference to FIGS. 3-8, the editor allows the user to build an autoverification rule as a flowchart shown on a graphical user interface. The user may easily insert new nodes as well as replace existing nodes in order to build the desired rule. In addition, the user may easily manipulate edges extending between nodes and define the node-to-node progression through the flowchart. The editor's flowchart-based language is generally intuitive and facilitates the user's expression of a desired autoverification procedure.

Creation and editing of autovalidation rules have been described above with respect to the "insert" option 141 and "replace" option 142. However, it will be recognized that numerous other options may be provided in the menu 122 or toolbar 124 for building and editing autoverification rules. For example, the select children option 143, which was not discussed above allows the user to specify subsequent nodes or "children" following an action node that does not automatically create edges and connected dummy nodes when placed in the rule builder window.

Another example of a tool that may be provided for the user is the ability to define node macros. Macros include a plurality of nodes connected in a certain order but not specifically associated with a particular autoverification rule. These macros may then be selected from a menu and inserted into different autoverification rules. In one embodiment, the macros are not configurable and can not be specialized for a particular rule. However, in another embodiment, some macros may be designed such that configuration and specialization for particular rule is possible. The "new procedure" option 132 from the top menu 122 may provide the user with the ability to create such macros.

Testing Autoverification Rules/Rule Check Environment

After an autoverification rule 100 is prepared, the autoverification rule will typically be tested before being used in the clinical laboratory. The present system provides a tool for such testing autoverification rules. FIGS. 9-16 provide an exemplary rule check environment provided by the system.

Figure 9:
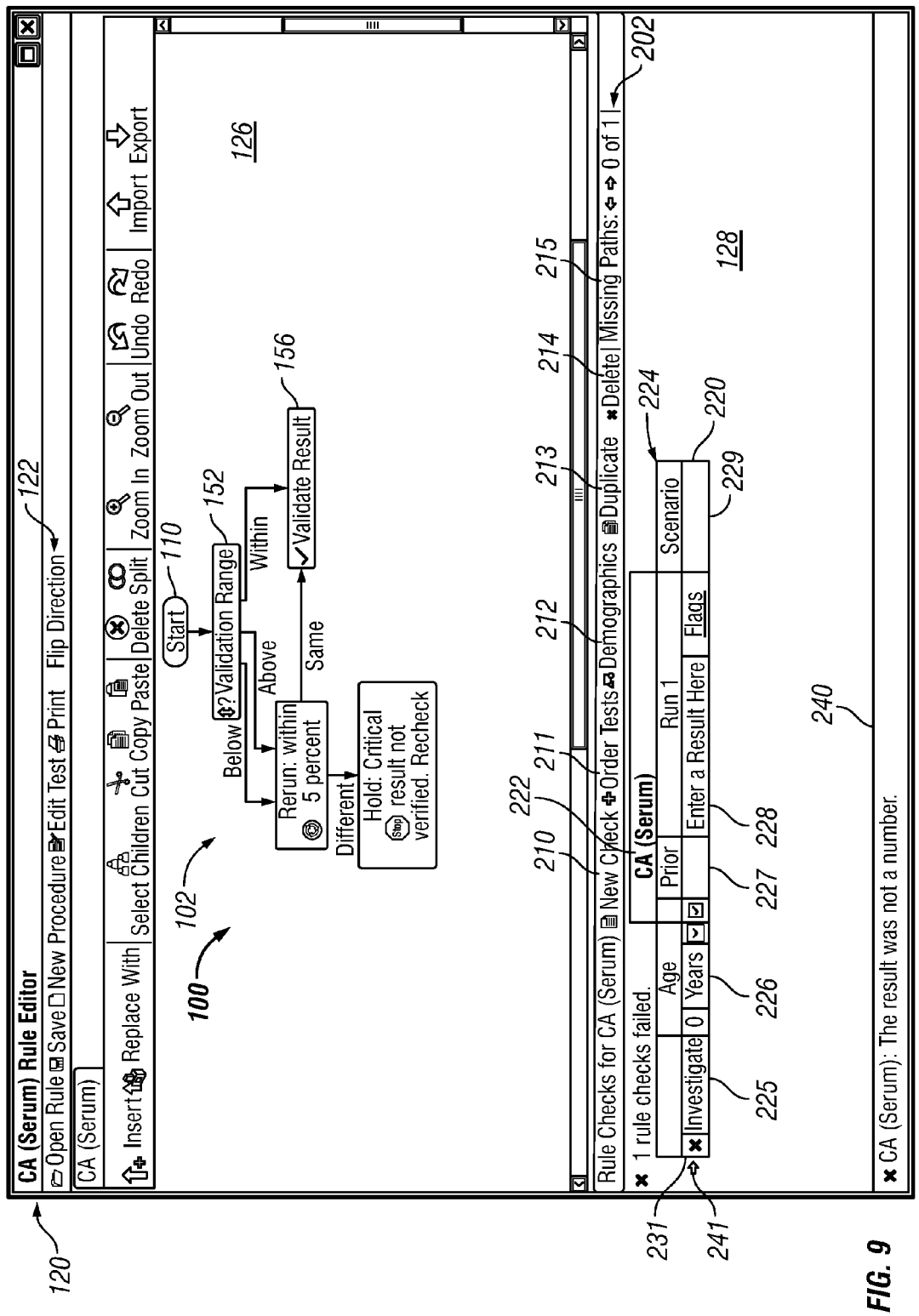
FIG. 9 shows a rule check table associated with the exemplary flowchart of FIG. 8.

With reference to FIG. 9, an exemplary autoverification rule 100 is shown in the rule builder window 126. After creating an autoverification rule, the user uses the rule check window 128 in combination with the rule builder window 126 to perform a rule check in the rule check environment of the system.

A rule check toolbar 202 is provided across the top of the rule check window 128. The rule check toolbar provides several options to the user, including a "new check" option 210, an "order tests" option 211, a "demographics" option 212, a "duplicate" option 213, a "delete" option 214, and a "missing paths" option 215.

To begin a rule check, the user clicks the "new check" option 210, and a table 220 appears in the rule check window 128. The table 220 includes a title block 222 indicating the autoverification rule related to the table. In the example of FIG. 9, the table 220 is related to the serum calcium autoverification rule. The table 220 also includes a header row 224 listing a plurality of column headings. In the exemplary embodiment of FIG. 9, the table includes a status column 225, an "age" column 226, a "prior" test result column 227, a "run 1" test result column 228, and a "scenario" column 229. Below the header row 224 in the table 220 are one or more rows, each row containing a single rule check for the autoverification rule shown in the rule builder window 126. As shown in FIG. 9, when the "new check" option 210 is initially selected, only a single row 231 is provided in the table 220. However, each time the "new check" option 210 is selected, an additional row appears in the table 220, providing an additional rule check for the autoverification rule.

As shown in FIG. 9, the user is invited define the rule check by entering an example input in the form of an exemplary test result in column 228 of the table 220 to define the rule check. In order to draw the user's attention to this column 228 and its instruction, the column 228 or its text may be highlighted. For example, the column 228 may appear in yellow color or with flashing text.

In addition to information provided in the table itself, an instruction bar 240 appears at the bottom of the rule check window 128 and provides additional information concerning the table 220. An arrow 241 appears next to the row of the table 220 that relates to the current information in the instruction bar 240. In the example of FIG. 9, the arrow 241 is located next to rule check 231 and the instruction bar 240 indicates that a numerical value should be entered in column 228 as an example test result for the rule check. In some situations, additional rule check data in addition to the example test input may be required, such as exemplary demographic information or exemplary prior test results.

Figure 10:
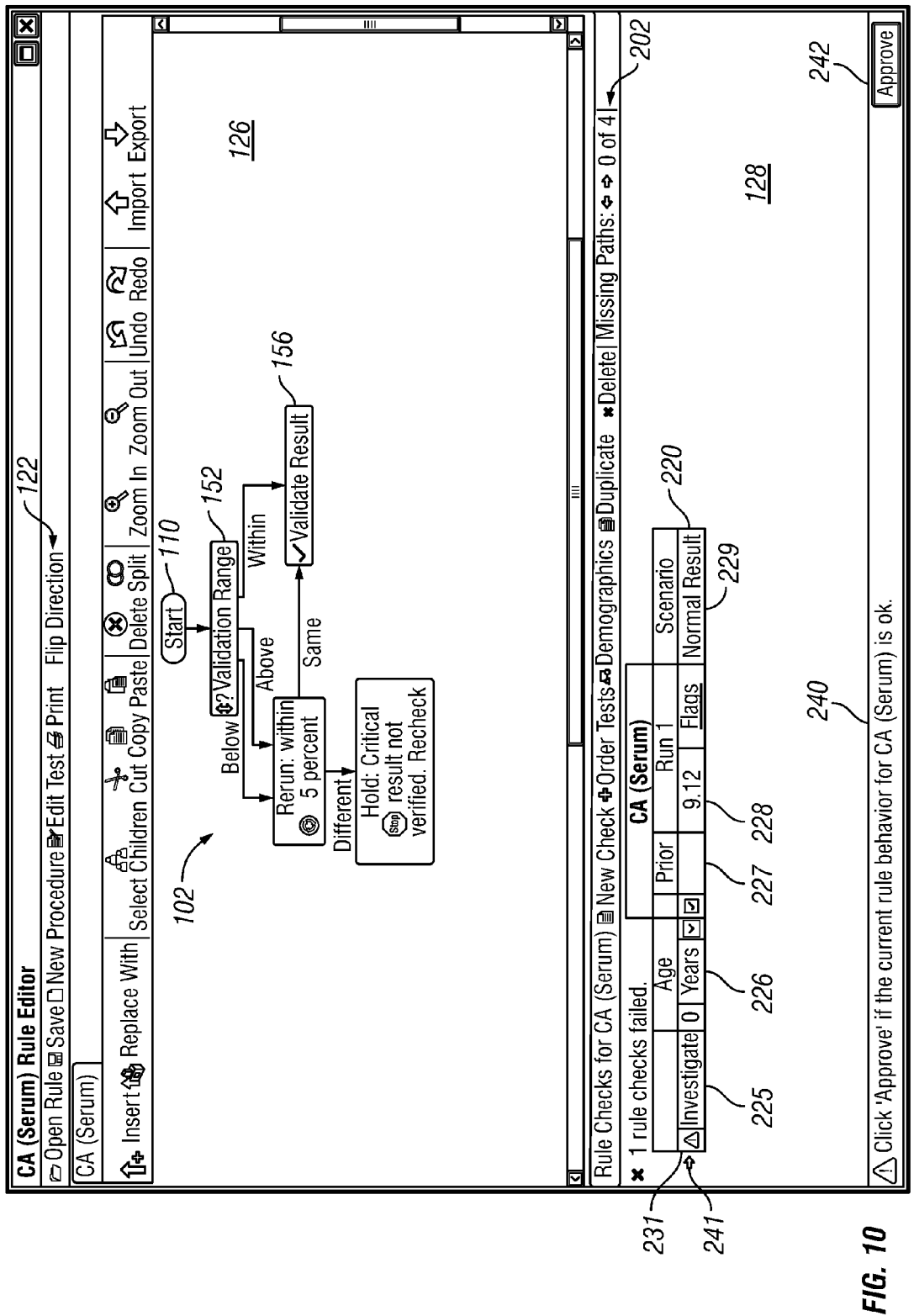
FIG. 10 shows entry of an example test result for a rule check in the rule check table of FIG. 9.

With reference now to FIG. 10, the user has inserted a numerical value of "9.12" in column 228, indicating that the example test result for the rule check of row 231 in 9.12 mg/dL. When the user inputs an example test result for a rule check in column 228, a comment may also be entered by the user in the scenario column 229. The comment in the scenario column will typically indicate the intended purpose of the rule check. For example, in FIG. 10, the user has entered the words "normal result" in the scenario column 229, indicating that the example test result value of "9.12" in column 228 is indicative of a normal serum calcium test result.

When the required rule check data is entered into the table 220 of the rule check window 128, the system automatically runs the autoverification rule using the rule check data and provides a rule check output. The rule check output indicates the side effects of the autoverification procedure on the system, including any final action resulting from the autoverification procedure, such as validation of the example test result. Other examples of rule check outputs include instructions to run additional tests, dilute the sample, hold the test result for further review, cancel a test, add a comment, modify a test result, or have the tech run a manual protocol. It will be recognized that numerous other rule check outputs are also possible.

In the example of FIG. 10, the rule check output can be seen by reviewing the action nodes in the rule check's path through the flowchart. To assist the user in following the rule check's path through the flowchart, the path is highlighted in the rule builder window 126. The highlighted path of the rule check is shown by highlighting the node-to-node progression of the rule check through the flowchart, which progression includes the nodes used in the rule check and the edges connecting such nodes. Highlighting the node-to-node progression may be accomplished in various ways, such as providing the nodes and edges in the path in a different color than the rest of the flowchart. For example, in FIG. 10, the start node 110, the range node 152, and the validate result node 156, along with their connecting edges may be shown in green, while the remaining nodes and edges in the flowchart 102 may be shown in blue.

With the rule check's path through the autoverification rule shown in the rule builder window 126, the table 220 provides a notice in column 225 asking the user to investigate the node-to-node progression of the rule check. For example, the notice to investigate may be provided by highlighting the column 225 of the row 231 in red and including the word "investigate" in the column. At the same time, the instruction bar 240 instructs the user to click the approve button 242 at the end of the instruction bar if the rule behavior for the rule check is the expected behavior.

Figure 11:
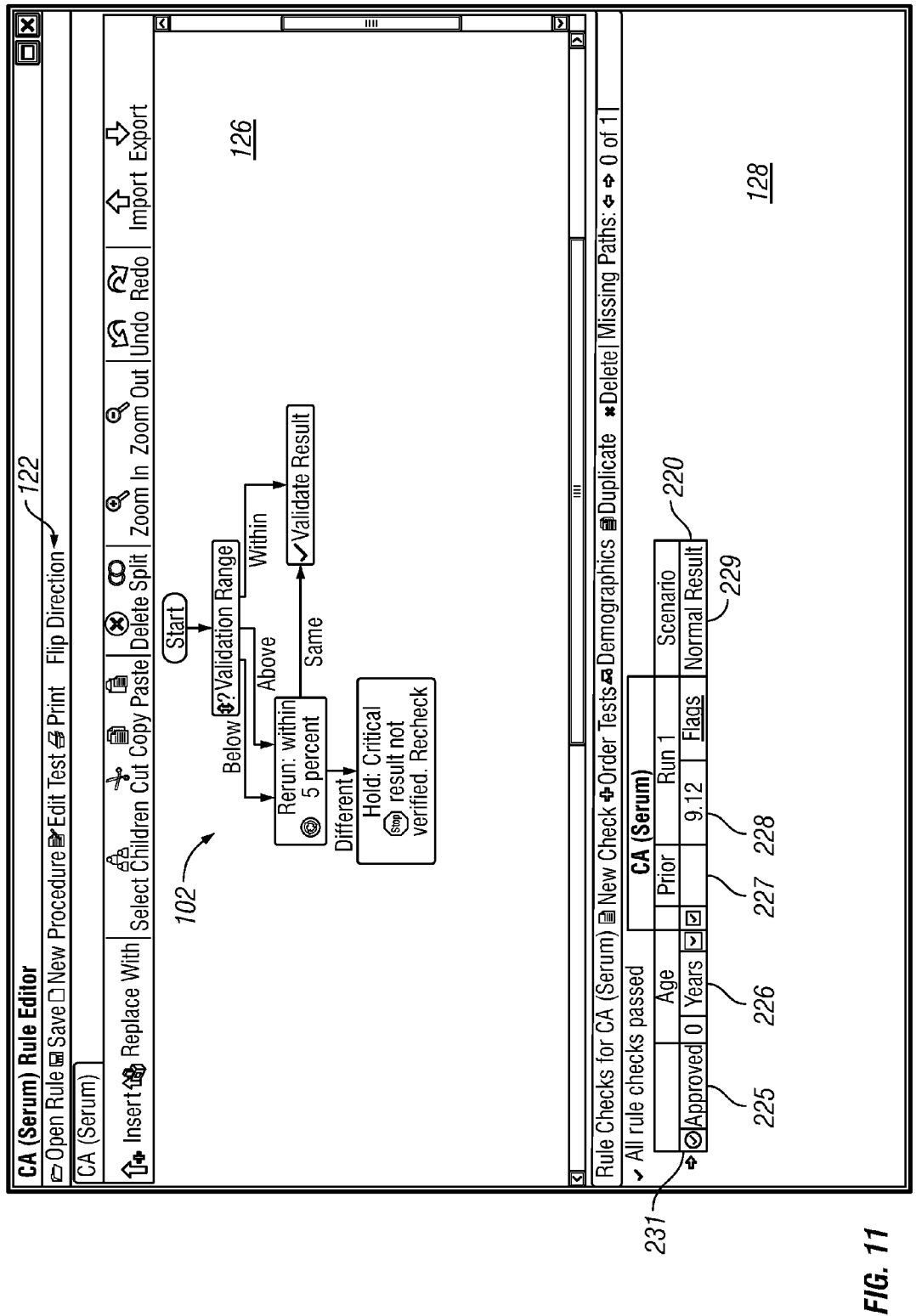
FIG. 11 shows approval of the rule check of FIG. 10, and a highlighted node-to-node progression of the rule check.

If the autoverification rule provides an expected output for the rule check, the user clicks on the approve button 242. An expected output is one in which the system response is appropriate based upon the entered test result. Once the approve button 242 is selected, the rule check is listed as approved in the rule check window 128. For example, as shown in FIG. 11, the word "approved" is included in column 225 for the rule check of row 231.

Figure 12:
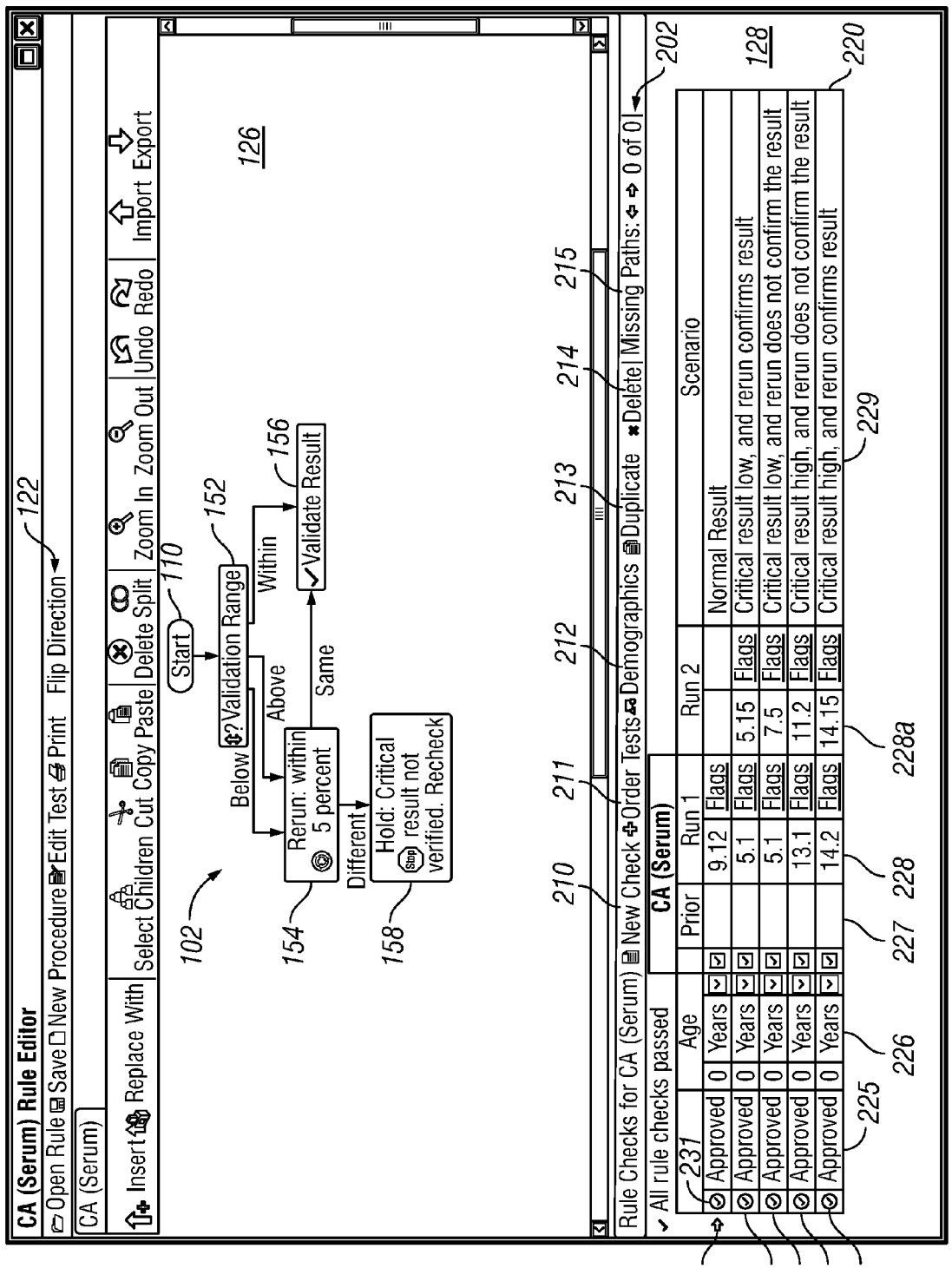
FIG. 12 shows the table of FIG. 11 expanded to include additional rule checks.

Multiple rule checks will be required to properly test all possible paths through an autoverification rule. With reference to FIG. 12, in order to submit additional rule checks for the autoverification rule shown in the rule builder window 126, the user selects the "new check" option 210 from the rule check toolbar 202. When this option 210 is selected, a new row appears in the table 220, and the user populates the new row with the desired data for the rule check. In FIG. 12, the user has included a total of five rule checks in the table, as shown in rows 231-235. The user has also approved each of these rule checks, as noted in column 225 of the table 220. The five rule checks 231-235 shown in FIG. 12 contemplate all possible paths through the flowchart 102 shown in the rule builder window 126. When all of the rule checks provided by the user have been approved, the autoverification rule is released for use in the laboratory with actual test results.

Another option for the user when creating new rule checks is to select the "duplicate" option 213 from the rule check toolbar 202. To use this option, the user highlights one row in the table and then clicks on the "duplicate" button 213. This results in a second row appearing in the table which is identical to the highlighted row. The user may then edit the second row to provide a new rule check for the displayed autoverification rule. The "duplicate" option 213 is useful when only minor changes are needed between rule checks, thus limiting the amount of input data required for the rule check.

Yet another option for the user when editing rule checks is the "delete" option 14. This option 214 allows the user to completely remove a rule check from the table 220.

In certain situations, the creation of a new rule check will require additional exemplary data that was not required for other rule checks already shown in the table 220. In these situations, a new column for the additional exemplary data must be inserted into the table 220 by the user. Two example options for adding new columns include the "order tests" option 211 and the "demographics" option 212.

The "order tests" option 211 allows the user to add columns to the table 220 which provide additional simulated test results for the rule check. For example, in FIG. 12, the user may select the "order tests" option 211 in order to add additional test results to the table 220 if the defined rule 100 is dependent upon such additional test results. With such additional test results inserted in the table 220, the complete path through the autoverification rule 100 can be shown in the rule builder window 126 for the rule check.

It will be noted that the creation of a new column does not require the entry of new data for all rule checks. For example, in FIG. 12 the first rule check 231 did not progress through node 154, so it did not require an example rerun test value in column 228a. Accordingly, this column 228a remains blank in for the first rule check 231 in FIG. 12.

Another example of a situation where a new column may be created in the table 220 is for additional demographic data for the rule check. When the user clicks the "demographics" option 212, the user may select additional demographic data for addition to the table 220, such as data related to the patient's sex or race. Depending on the autoverification rule being checked, this additional data may be optional or mandatory to the rule check.

In the above exemplary embodiments, additional columns are manually added to the table 220 by the user. However, the system may also be configured to automatically add columns to the table 220 when required by the autoverification rule and associated rule check. For example, in FIG. 12, the system may be configured to automatically add the rerun column 228a when a rule check is created with a path that will go through rerun node 154. Thus, when the user enters a "Run 1" test result of "5.1" in column 228, the system recognizes that this test result is below the validation range defined in node 152 of the autoverification rule, and progresses to the rerun node 154 according to the defined autoverification process. Requiring an exemplary rerun test result from the rule check, the system then creates the additional column 228a in the table 220, and indicates that a "Run 2" example test result should be entered in this column 228a. In the example of FIG. 12, the user entered a value of "5.15" in the column 228a.

After an autoverification rule is created, tested and implemented in the laboratory, the laboratory may decide that revisions to the autoverification rule are necessary. In particular, the laboratory may find that additional workflow or analysis on a test sample would provide a better autoverification rule for a particular test. As described previously, autoverification rules may be easily edited from the rule builder window 126. In order to edit a particular test, the user selects the "open rule" option 130 from the top menu 122 and selects the autoverification rule to edit. The flowchart for the autoverification rule then appears in the rule builder window 126, and the flowchart may be easily edited by adding nodes and edges, deleting nodes and edges, or changing node configurations.

Figure 13:
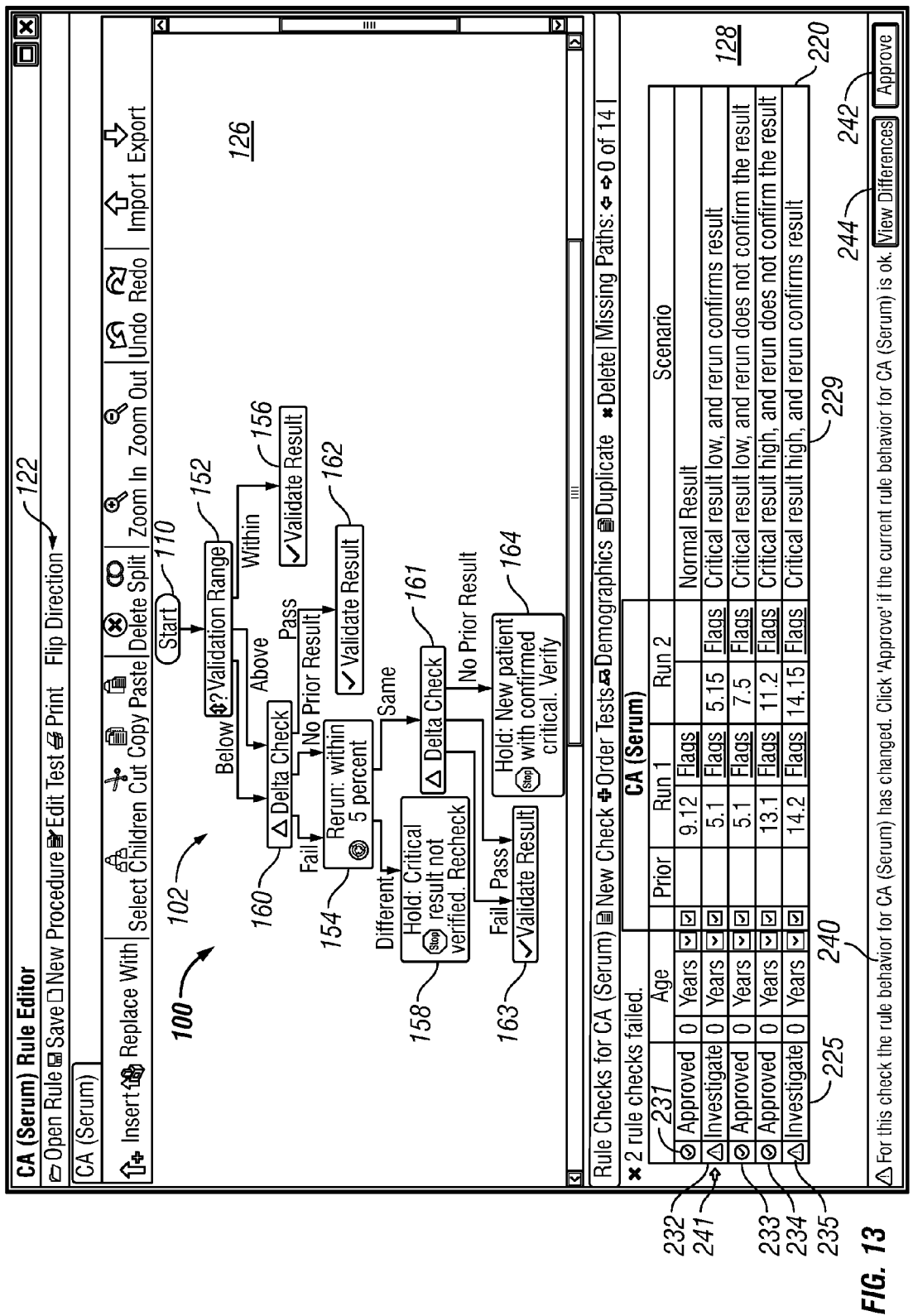
FIG. 13 shows a modified autoverification rule from that of FIG. 12 and the resulting rule check changes in the rule check table.

When an existing autoverification rule is modified, the outputs associated with rule checks for the autoverification rule may also change. When this happens, the user is asked to approve the modified rule check outputs before the modified autoverification rule is approved and released for actual use. FIG. 13 shows an example of this situation.

In FIG. 13, the autoverification rule previously shown in FIG. 12 has been edited to include additional nodes and edges. In addition to the previous nodes, the flowchart 102 for the modified autoverification rule 100 now includes first and second delta check nodes 160, 161, second and third validation nodes 162, 163, and an additional hold node 164.

As shown in the rule check window 128, by editing the autoverification rule 100, rule checks 232 and 235 now have different rule outputs which have not been approved. Accordingly, rule checks 232 and 235 are highlighted in column 225 of the table 220 and include an instruction to "investigate" the rule check. At the same time, the instruction bar 240 tells the user that the rule check's behavior has changed based on edits to the serum calcium rule, and that such behavior needs to be approved.

Figure 14:
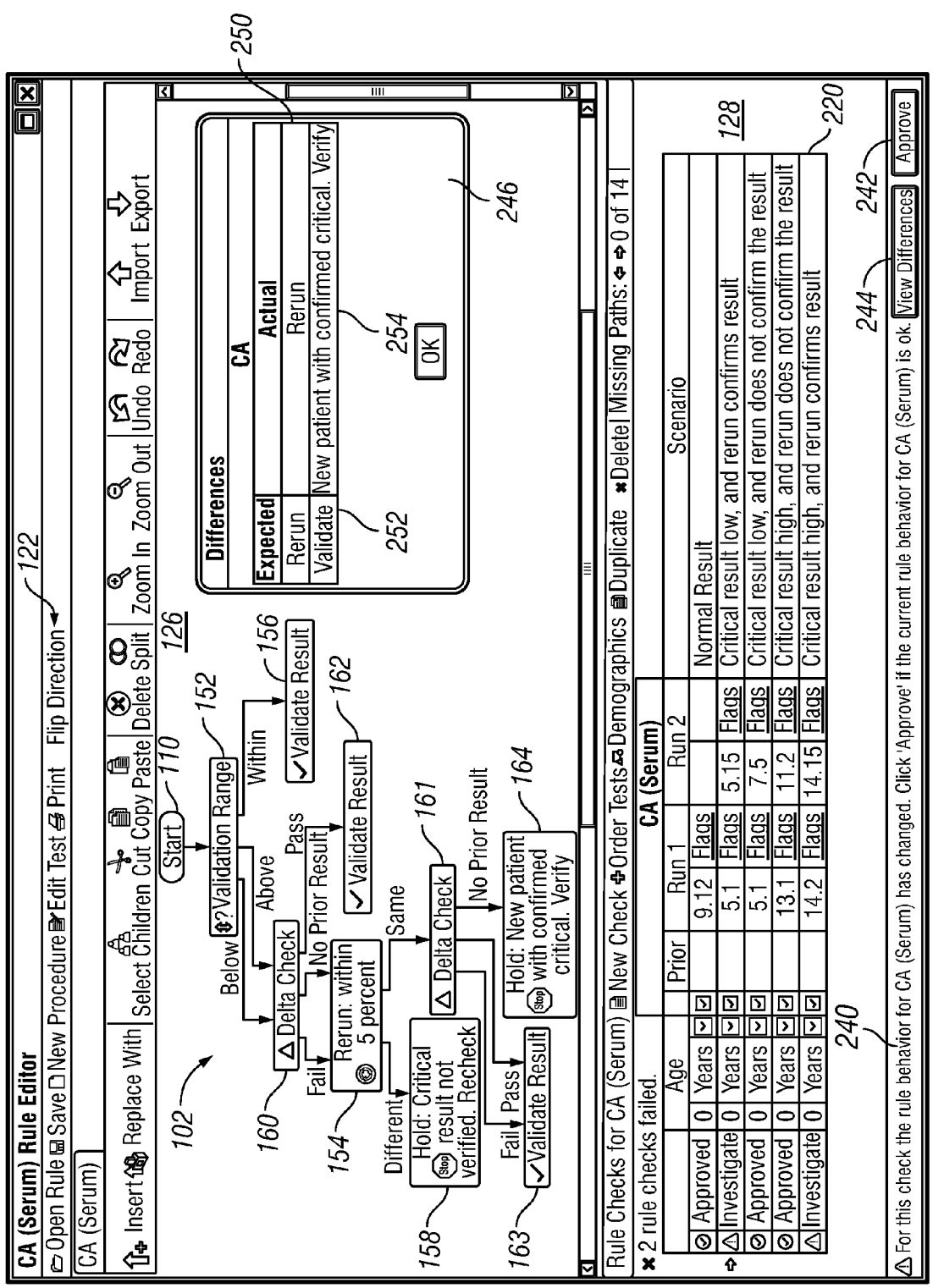
FIG. 14 shows a differences window highlighting the differences in the rule check output from the original version of the rule shown in FIG. 12 to the modified version of the rule.

To assist the user in approving changes to rule check behavior, a "view differences" button 244 is provided on the instruction bar 240. When the "view differences" button is selected, the user is presented with a differences window 246, such as that shown in FIG. 14. The differences window 246 shows the differences between the original outputs for the rule check and the new outputs for the rule check following the edits to the rule. In the example of FIG. 14, this information is provided in the table 250. The table 250 includes an "expected" column 252 and an "actual" column 254. The "expected" column 252 shows the originally approved outputs for the rule check from the previous version of the rule check. In this case, the original outputs included the rerun side effect from the rerun node 154 and the validate side effect from the validate node 156. The "actual" column 254 shows the rule check outputs for the modified version of the rule. In this case, the new rule check outputs include the same rerun side effect from the rerun node 154, and also include a different side effect in the form of a hold from the hold node 164. The different side effect outputs are highlighted in red in the second row of the table to emphasize the difference in the outputs. Accordingly, with the differences window 246, the user is provided with a convenient tool that quickly emphasizes differences in the rule checks resulting from the edited autoverification rule.

Figure 15:
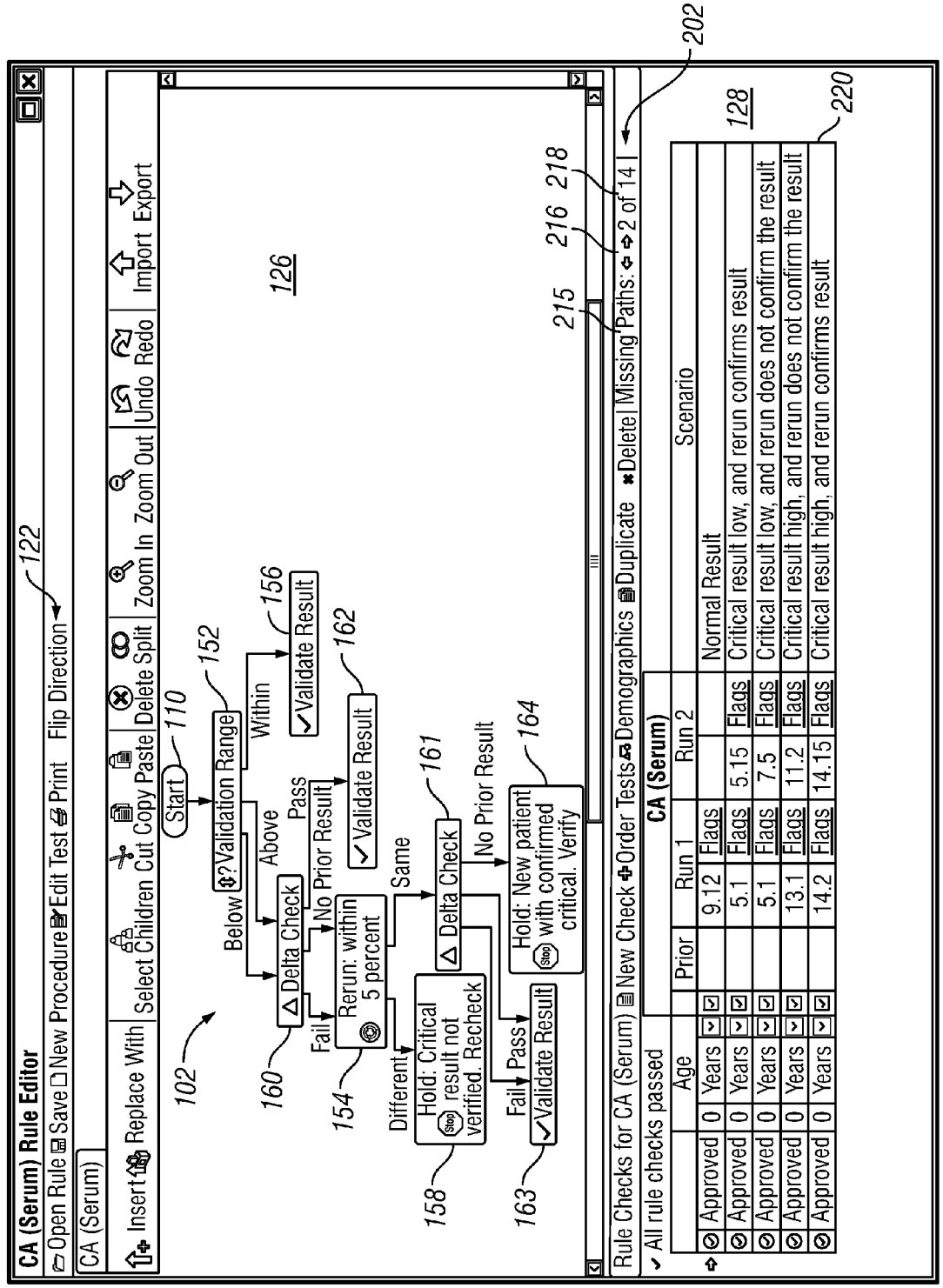
FIG. 15 shows a highlighted path through the modified rule of FIG. 13 for which no rule check exists in the rule check table.

With reference now to FIG. 15, when a user reviews rule checks for a new or modified autoverification rule, the missing paths option 215 may be selected to help the user provide rule checks for all paths through the autoverification rule. When the missing paths option is selected, the system determines how many potential paths through the flowchart 102 do not have an associated rule check in the table 220. The first of these missing paths is then highlighted in the flowchart 102 in the rule builder window. For example, a missing path may be highlighted by providing the edges for the path in red and bordering the associated nodes in red. The remaining edges in the flowchart may remain in black along with black outlines around the remaining nodes. In the example of FIG. 15, the highlighted missing path includes the following nodes and edges: the start node 110, the range node 152, the "above" output edge, the delta check node 160, the "fail" output edge, the rerun node 154, the "same" output edge, the delta check node 161, the "pass" output edge, and the validate result node 163.

When the user is presented with a missing path, the user may build a rule check for the missing path in the table 220. The total number of missing paths for the flowchart 102 displayed in the rule builder window 126 is shown on the rule check toolbar 202 at box 218. The user may sequentially display such missing paths from the first to the last using the arrows provided in box 216. In particular, each time the forward arrow is selected, the next missing path will be highlighted in the flowchart 102. Each time the reverse arrow is selected, the previous missing path will be highlighted in the flowchart 102.

Figure 16:
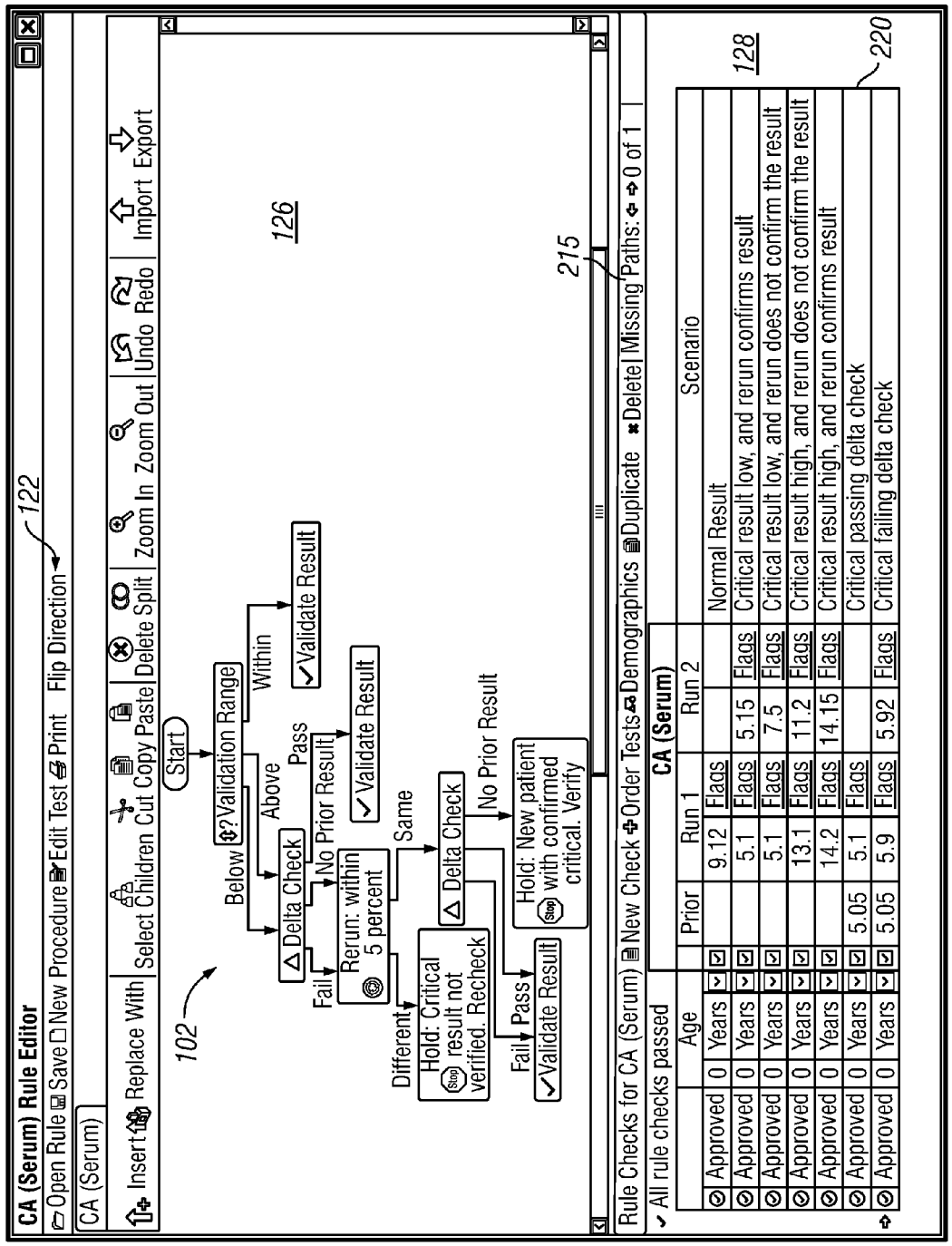
FIG. 16 shows additional rule checks included in the rule check table of FIG. 15 based on the missing paths highlighted by the system.

As shown in FIG. 16, the user has added and approved two additional rule checks from FIG. 15 based on the missing paths made available to the user. With all rule checks approved, the autoverification rule is available for use in the laboratory. Advantageously, the user may print the flowchart 102 and table 220 of rule checks to provide documentation of the rule check procedures used on a given autoverification rule before the rule was released to the laboratory. In addition, the rule checks for any given autoverification rule will be saved in the system's data storage should the rule checks need to be viewed in the future.

Execution of Autoverification Rules/Laboratory Environment

Once an autoverification rule is created along with its rule checks, the rule is saved by the system in data storage 20 (see FIG. 1) and is available for execution by the processor 16 when a test order associated with the autoverification rule is received in the laboratory. A test order typically includes at least one test to be run by a laboratory analyzer and data related to the patient associated with the test order (e.g., name, age, sex, weight, height, etc.). Test orders may be received automatically via a computer network, or may be manually entered into the system by a laboratory technician. When a test order is received by the laboratory it is accompanied by a test sample. The test sample is delivered to the appropriate laboratory analyzer (or manual analyzer station) so the designated test can be performed on the sample. Upon receipt of a test order, the system operates in a laboratory environment where actual clinical test results are verified using the autoverification rules.

Execution of an autoverification rule associated with a test order begins when the system receives the test order. Upon receipt of the test order, the system pulls the saved autoverification rule from memory or data storage and proceeds with execution of the rule.

Execution of each rule begins with the start node. Thereafter, the rule proceeds from node-to-node 104 as directed by the edges 106. When reaching a new node, the system calls the routines associated with the node including any logic and side-effects. Upon performing the routines associated with the node 104, the defined rule indicates whether the system should stop rule execution, wait for a new result, or follow one of the output edges 106 from the node to a new node 104 and begin execution of the new node. When the rule reaches an action node with no output edges, the rule terminates. The rule does not execute again until a new test order calling for the rule is received. If desired, the user may display the flowchart representation 102 of the autoverification rule on the graphical user interface 14 during execution. However, in most instances, the processor will execute the rule without displaying it on the graphical user interface.

The laboratory will typically receive multiple test orders for multiple samples at one time. Accordingly, the processor 16 may run multiple autoverification rules in parallel. This may include simultaneously running two or more instances of the same autoverification rule on two or more different test orders and/or simultaneously running two or more different autoverification rules on two or more different test orders.

As mentioned above, during the execution process an autoverification rule may be suspended and instructed to wait. A typical example of a situation where a rule suspends is where a node can not be executed because necessary data is unavailable. For example, if the rule of FIG. 8 is executed, the rule must wait at node 152 to receive a serum calcium test result from the laboratory analyzer before moving on to subsequent nodes 154 or 156. Thus, when a test order for serum calcium is received, the rule suspends at node 152 until the laboratory analyzer produces the serum calcium test result. In this situation, a rule will suspend indefinitely until it receives the serum calcium test result or is cancelled by the user. If a rule is terminated by the user, the system generates an error notice. The test result is then passed on to the laboratory technician for handling. The technician can then manually determine whether the test result is valid.

FIG. 8 also provides another example of a situation where a rule may suspend. Upon reaching the rerun node 154, the previously executed test is re-ordered by the system, and the rule is suspended until the new test result is received. In order to accomplish this, the system may issue a notification to the laboratory technician to place the sample tube back on the laboratory analyzer. Alternatively, if the system includes robotics or some other mechanized sample transportation device, the system may automatically rerun the test through the laboratory analyzer and the laboratory technician would not be notified at all. In this situation, the rerun is handled entirely by the system.

Although the present invention has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of the appended claims should not be limited to the description of the preferred embodiments contained herein.

What is claimed is:

1. A system for testing the performance of an autoverification rule, the system comprising:
an output device that displays a graphical user interface configured to display the autoverification rule as a flowchart comprising a plurality of nodes and edges, the plurality of nodes including a start node and one or more output nodes, wherein the flowchart further comprises a plurality of paths, each path being a different node-to-node progression through the flowchart from the start node to one of the one or more output nodes, wherein the progression includes the nodes used in the path and the edges connecting such nodes, the output nodes comprising at least one of a validate node and a hold node; and
a processor configured to perform the autoverification rule on rule check data, the autoverification rule being configured to automatically evaluate laboratory test results, the rule check data including an example test result,
wherein the processor is further configured to identify on the graphical user interface which one of the plurality of paths was taken by the processor in performing the autoverification rule on the rule check data.

2. The system of claim 1 wherein the processor is further configured to automatically perform the autoverification rule on the rule check data whenever the autoverification rule is modified.

3. The system of claim 1 wherein the processor is further configured to:
perform the autoverification rule on a plurality of sets of rule check data;
determine whether the paths taken by the processor in performing the autoverification rule on each of the sets of rule check data account for each possible path through the flowchart representation of the autoverification rule; and
indicate a path on the graphical user interface that is not accounted for in performing the autoverification rule on each of the sets of rule check data.

4. The system of claim 1 wherein the processor is further configured to automatically perform the autoverification rule on each of the plurality of sets of rule check data whenever the autoverification rule is modified.

5. The system of claim 1 wherein the rule check data further includes at least one of an exemplary demographic information and an exemplary prior test result.

6. The system of claim 1 wherein the nodes and edges of the identified path are presented in a different color than other nodes and edges in the flowchart.

7. The system of claim 1 wherein the processor produces rule check output when the processor performs the autoverification rule on the rule check data, the rule check output comprising at least one of validating the example test result, holding the example test result for manual review, ordering a further test, rerunning a prior test, cancelling an existing test, adding a comment, and modifying the test result.

8. A method of testing an autoverification rule, the method comprising:
displaying the autoverification rule as a flowchart including a plurality of nodes and edges on a graphical user interface, the nodes comprising at least one of a validate node and a hold node, wherein the autoverification rule is configured to automatically evaluate laboratory test results;
receiving an example laboratory test result as input to test the autoverification rule;
performing, by a processor, the autoverification rule on the example laboratory test result to determine an autoverification output; and
identifying, by the processor, a path through the displayed plurality of nodes and edges representing actions of the autoverification rule performed by the processor to determine the autoverification output, wherein the identified path is one of a plurality of different paths from input to output through the displayed plurality of nodes and edges.

9. The method of claim 8 further comprising the step of receiving a user input approving the autoverification output and storing an indication that the autoverification output has been approved.

10. The method of claim 9 further comprising the step of displaying a table including a listing of the example laboratory test result and the indication that the autoverification output has been approved.

11. The method of claim 9 further comprising the step of saving the indication that the autoverification output has been approved as proof of testing of the autoverification rule.

12. The method of claim 8 wherein after the autoverification rule is modified, the processor automatically performs the modified autoverification rule on the example laboratory test result to determine if the autoverification output has changed for the example laboratory test result.

13. The method of claim 12 wherein the processor automatically indicates whether the modification to the autoverification rule results in a changed autoverification output.

14. The method of claim 13 wherein the processor automatically indicates whether the modification to the autoverification rule results in a changed autoverification output by simultaneously displaying the autoverification outputs from the modified and unmodified autoverification rules for the example laboratory test result.

15. The method of claim 8 wherein the nodes and edges of the identified path are displayed in a different color from other nodes and edges in the flowchart.

16. The method of claim 8 further comprising the steps of:
(i) receiving one or more additional example laboratory test results;
(ii) performing by the processor the autoverification rule on each of the additional example laboratory test results; and
(iii) highlighting by the processor a missing path through the plurality of nodes and edges, wherein the missing path comprises a path not in performing the autoverification rule on all of the example laboratory test results.

17. A system for testing the performance of an autoverification rule, the system comprising:
an output device that displays a graphical user interface configured to display the autoverification rule as a flowchart comprising a plurality of nodes and edges, the plurality of nodes including a start node and one or more selectable nodes, wherein there are a plurality of paths through the flowchart, each of the paths being a different node-to-node progression through the flowchart of the autoverification rule from the start node to one of the one or more selectable nodes, the selectable nodes comprising at least one of:
an order test node that directs a laboratory analyzer to perform a test on the patient sample;

a rerun node that directs the laboratory analyzer to automatically rerun the test on the patient sample;

a range check node that determines if a value of a laboratory test result is inside, below, or above a validation range provided by the user based on the test and the laboratory analyzer; and a delta check node that retrieves a prior laboratory test result of the patient and compares the laboratory test result and the retrieved prior laboratory test result; and a processor configured to:

perform the autoverification rule on a plurality of sets of rule check data, wherein the autoverification rule is configured to automatically evaluate laboratory test results, determine if the paths followed by the processor in performing the autoverification rule on each of the sets of rule check data include each of the paths through the flowchart; and identify, on the graphical user interface, a missing path through the flowchart, wherein the missing path comprises a path not followed by the processor in performing the autoverification rule on each of the sets of rule check data.

18. The system of claim 17 wherein the processor is further configured to identify the missing path by displaying the nodes and edges of the missing path in a different color from other nodes and edges in the flowchart.

19. The system of claim 17 wherein the processor is further configured to identify the path followed by the processor in performing the autoverification rule on one of the sets of rule check data.

20. The system of claim 17 wherein the processor is further configured to provide a plurality of environments through the graphical user interface, the plurality of environments comprising:

i) an editor environment configured to edit the autoverification rule;

ii) a rule check environment configured to test the performance of the autoverification rule; and iii) a laboratory environment configured to perform the autoverification rule on clinical test results.

* * * * *